United States Patent
Kim et al.

(10) Patent No.: US 9,765,329 B2
(45) Date of Patent: Sep. 19, 2017

(54) ADIPOCYTE-TARGETING NON-VIRAL GENE DELIVERY SYSTEM

(71) Applicant: INDUSTRY-UNIVERSITY COOPERATION FOUNDATION HANYANG UNIVERSITY, Seoul (KR)

(72) Inventors: Yong-Hee Kim, Seoul (KR); Kwang-Suk Lim, Seoul (KR); Young-Wook Won, Seoul (KR); Jang-Kyoung Kim, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 14/784,491

(22) PCT Filed: Mar. 31, 2014

(86) PCT No.: PCT/KR2014/002718
§ 371 (c)(1),
(2) Date: Oct. 14, 2015

(87) PCT Pub. No.: WO2014/171646
PCT Pub. Date: Oct. 23, 2014

(65) Prior Publication Data
US 2016/0130579 A1    May 12, 2016

(30) Foreign Application Priority Data
Apr. 16, 2013 (KR) .................. 10-2013-0041402

(51) Int. Cl.
*A61K 38/08* (2006.01)
*C12N 15/113* (2010.01)
*A61K 48/00* (2006.01)
*C12N 15/11* (2006.01)

(52) U.S. Cl.
CPC ............ *C12N 15/113* (2013.01); *A61K 38/08* (2013.01); *A61K 48/0025* (2013.01); *C12N 15/111* (2013.01); *A61K 48/00* (2013.01); *C12N 2310/14* (2013.01); *C12N 2310/3513* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | |
|---|---|---|
| 6,306,993 B1 | 10/2001 | Rothbard et al. |
| 6,495,663 B1 | 12/2002 | Rothbard et al. |
| 2002/0131965 A1 | 9/2002 | Rothbard et al. |
| 2003/0162719 A1 | 8/2003 | Rothbard et al. |
| 2004/0176282 A1 | 9/2004 | Dalby et al. |
| 2006/0024692 A1 | 2/2006 | Nakamura et al. |
| 2006/0111274 A1 | 5/2006 | Rothbard et al. |
| 2006/0122118 A1 | 6/2006 | Ho |
| 2013/0295012 A1 | 11/2013 | Ingber et al. |

FOREIGN PATENT DOCUMENTS

| | | | |
|---|---|---|---|
| IL | WO 2012090150 A2 * | 7/2012 | ....... A61K 47/48238 |
| JP | 2002-502376 A | 1/2002 | |
| JP | 2006-517790 A | 8/2006 | |
| KR | 10-2009-0120948 A | 11/2009 | |
| WO | 2004/031413 A2 | 4/2004 | |
| WO | 2012/074588 A2 | 6/2012 | |

OTHER PUBLICATIONS

Kolonin et al., "Reversal of obesity by targeted ablation of adipose tissue", Nature Medicine, 2004; 625-632.*
Won et al., "Reducible Poly(oligo-D-arginine) for Enhanced Gene Expression in Mouse Lung by Intratracheal Injection", The American Society of Gene and Cell Therapy, 2010; 734-742.*
International Search Report issued Jul. 4, 2014 in PCT/KR2014/002718 filed Mar. 31, 2014.
Sara Trabulo et al., "Cell-Penetrating Peptides—Mechanisms of Cellular Uptake and Generation of Delivery Systems", Pharmaceuticals 2010, 3, pp. 961-993.
Yun-Hao Dai et al., "Gene Transport and Expression by Arginine-rich Cell-penetrating Peptides in Paramecium", Gene, 489 (2), Dec. 10, 2011, pp. 89-97.
Manoj Lakshmanan et al., "Rapid and Efficient Gene Delivery into Plant Cells Using Designed Peptide Carriers", Biomacromolecules, 2013, 14 (1), pp. 10-16.

* cited by examiner

*Primary Examiner* — Lianko Garyu
(74) *Attorney, Agent, or Firm* — Oblon, McClelland, Maier & Neustadt, L.L.P.

(57) ABSTRACT

The present invention relates to a gene delivery system for targeting adipocytes and a treatment system for obesity and obesity-derived metabolic syndromes using the same and, more particularly, to a non-viral gene delivery system which directly targets a differentiated obesity (mature) adipocyte and contains an adipocyte targeting sequence (ATS)-arginine (R9) peptide.

10 Claims, 21 Drawing Sheets

[Fig. 1]
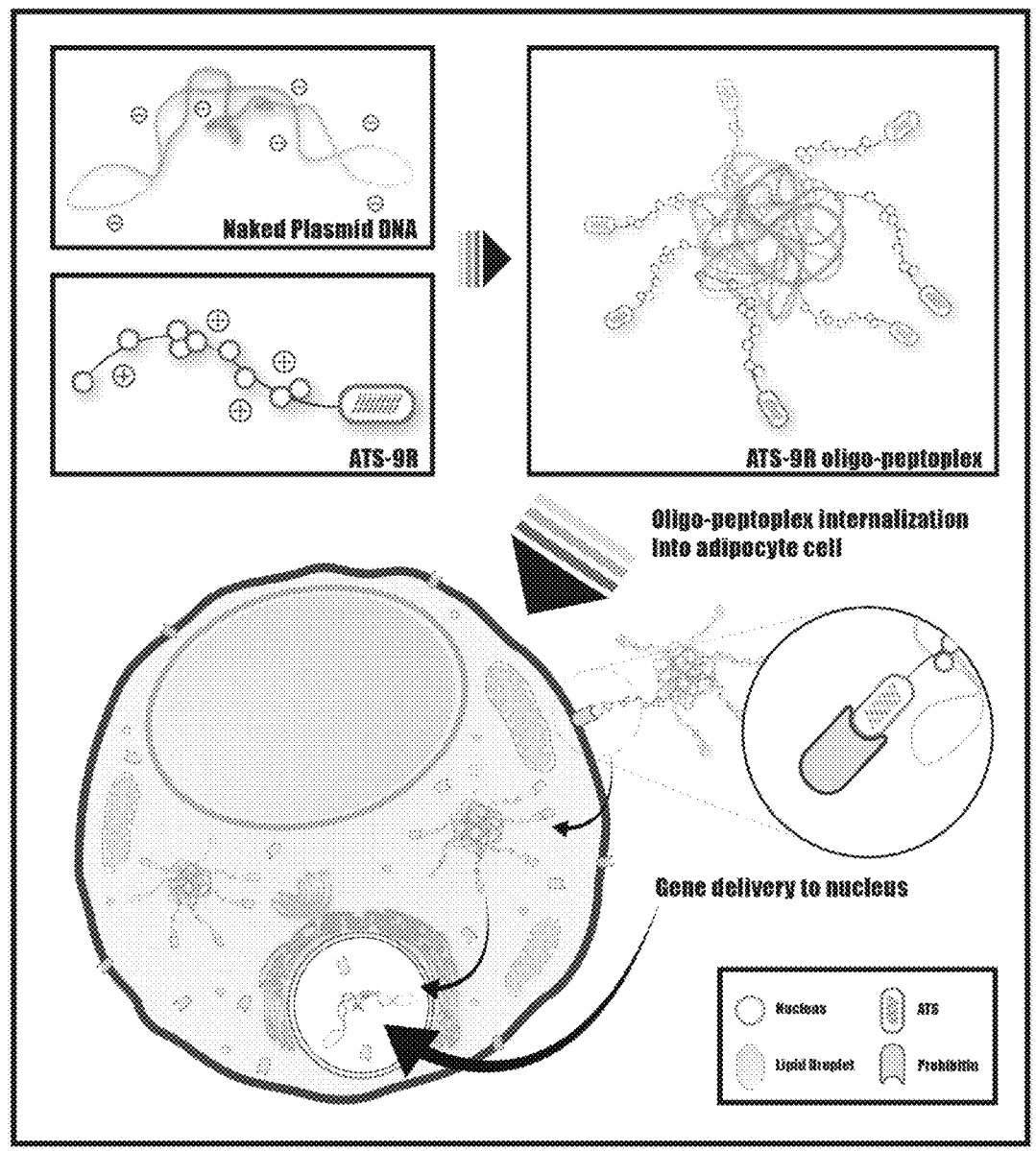

[Fig. 2]
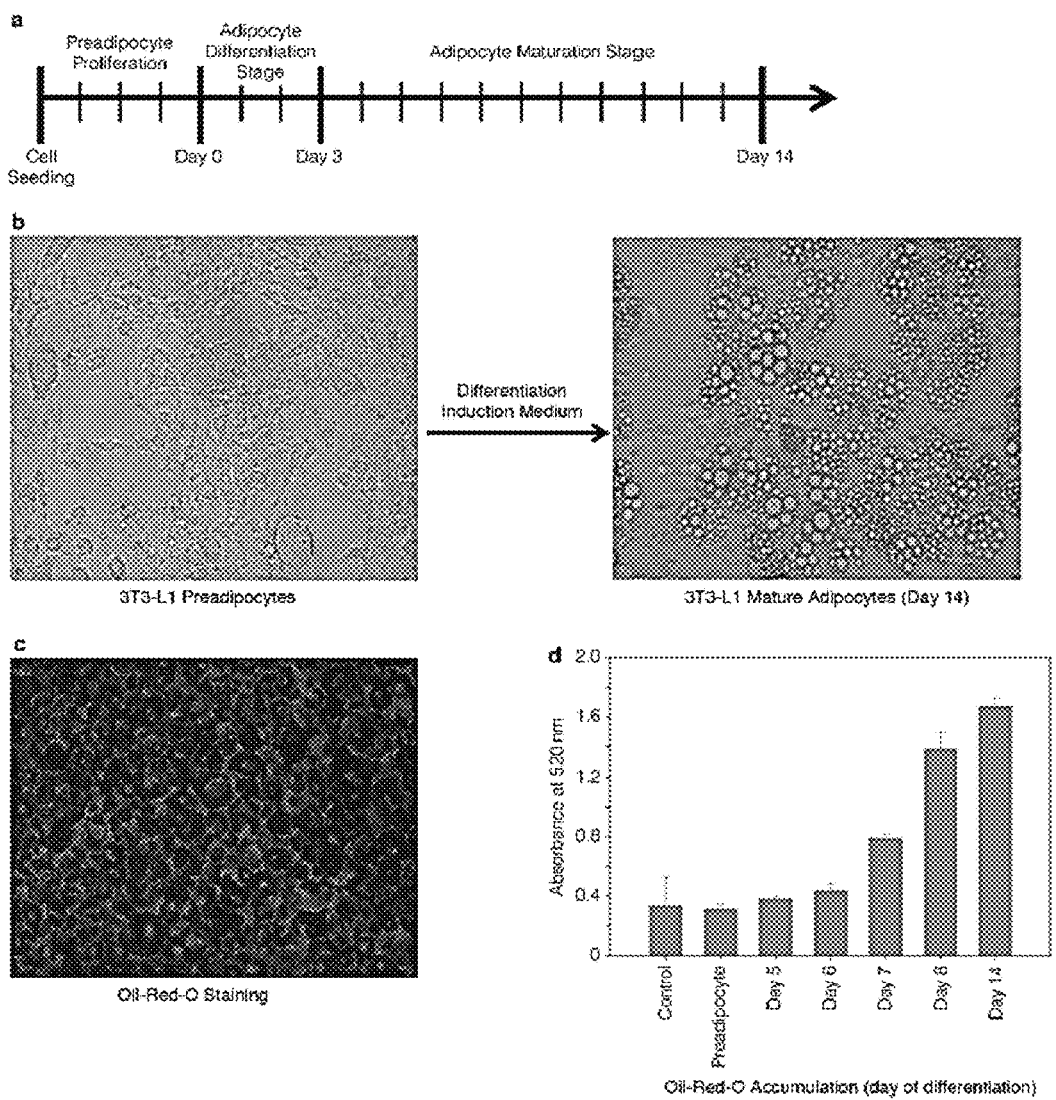

[Fig. 3]
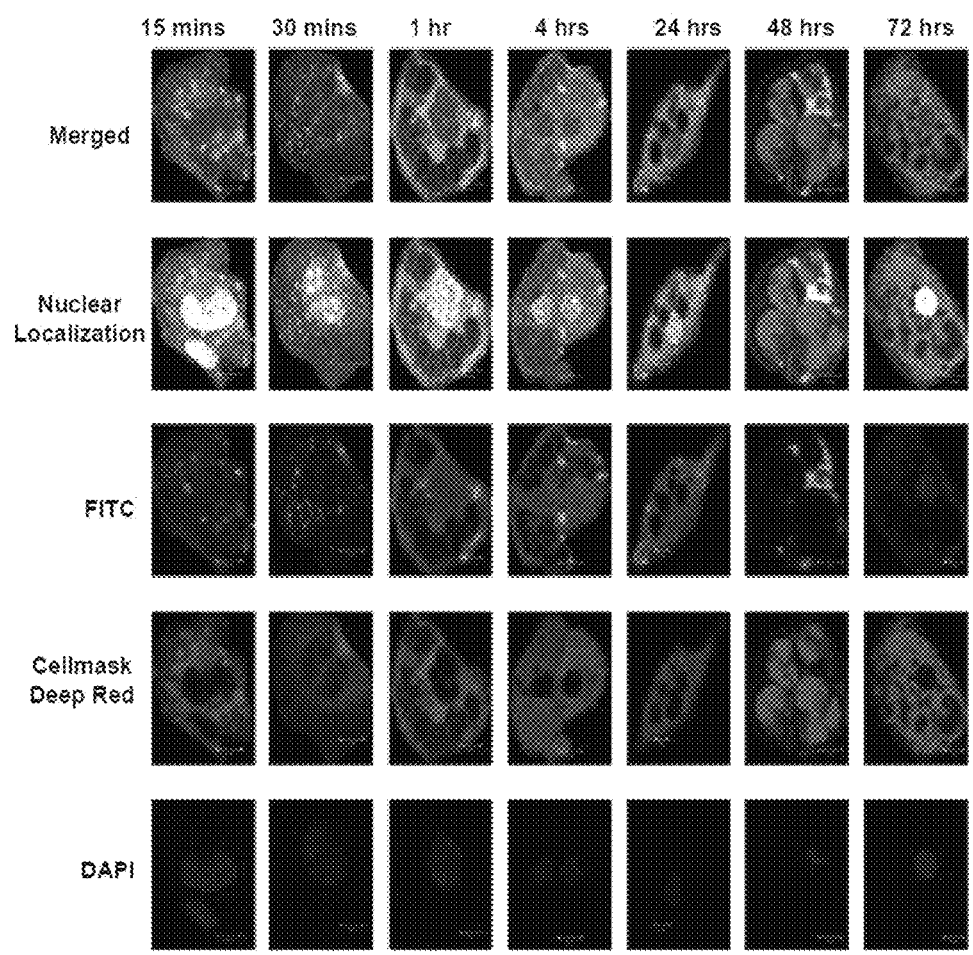

[Fig. 4]
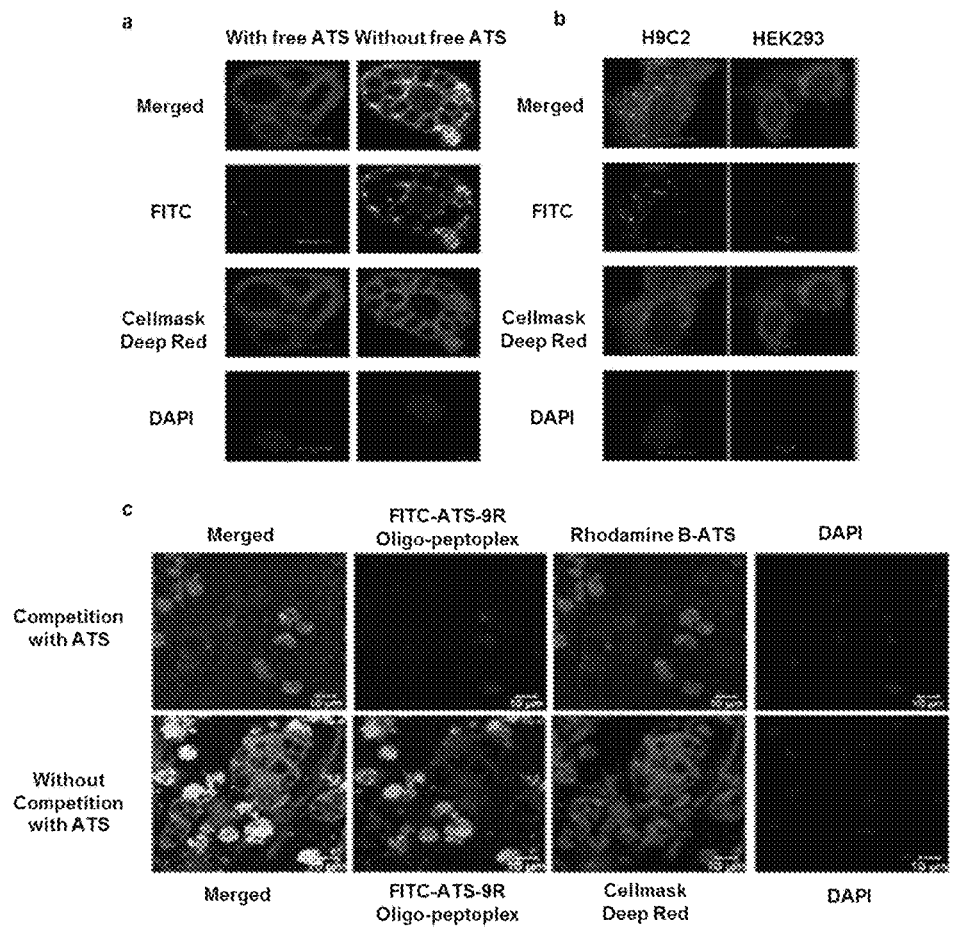

[Fig. 5]
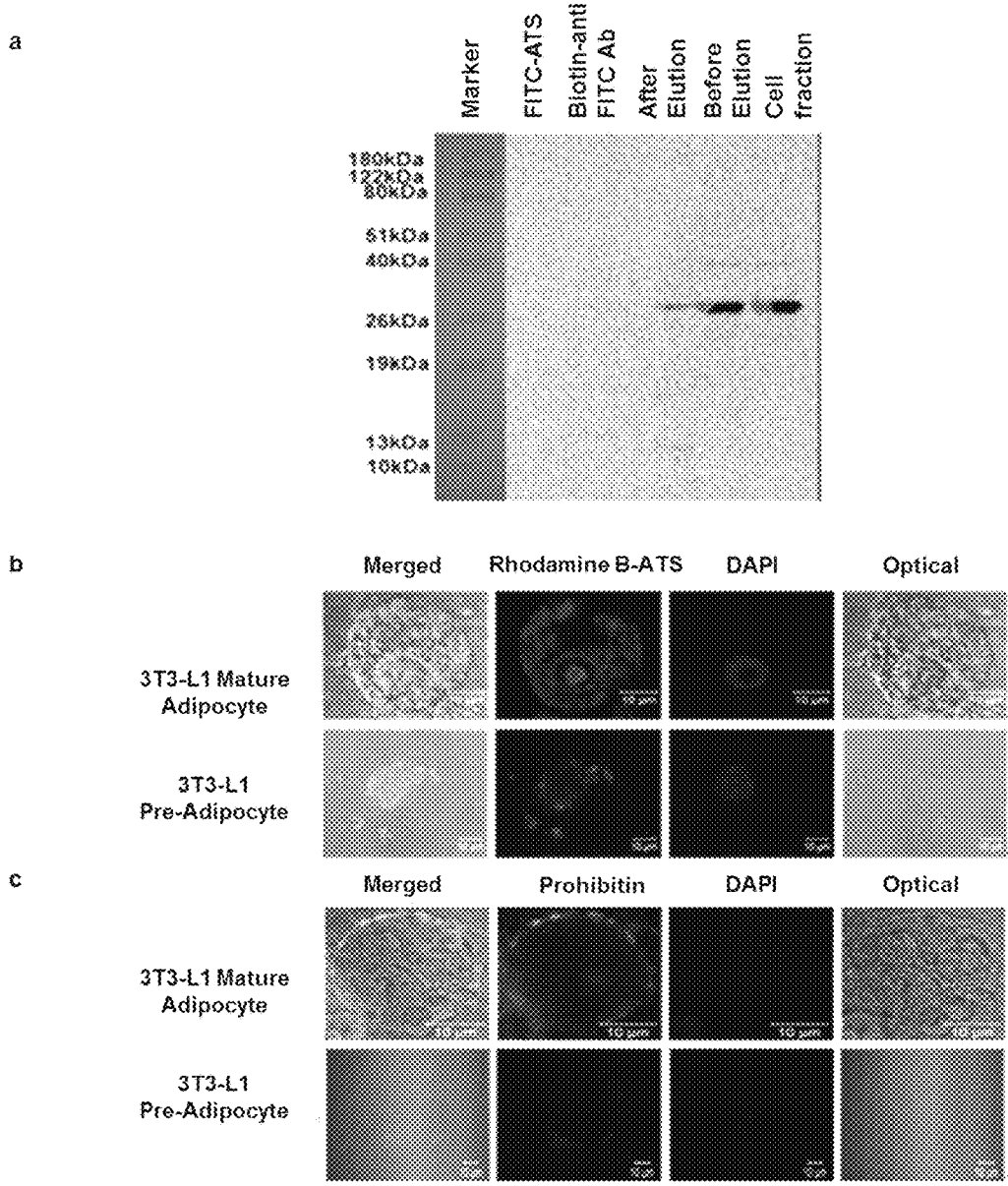

[Fig. 6]
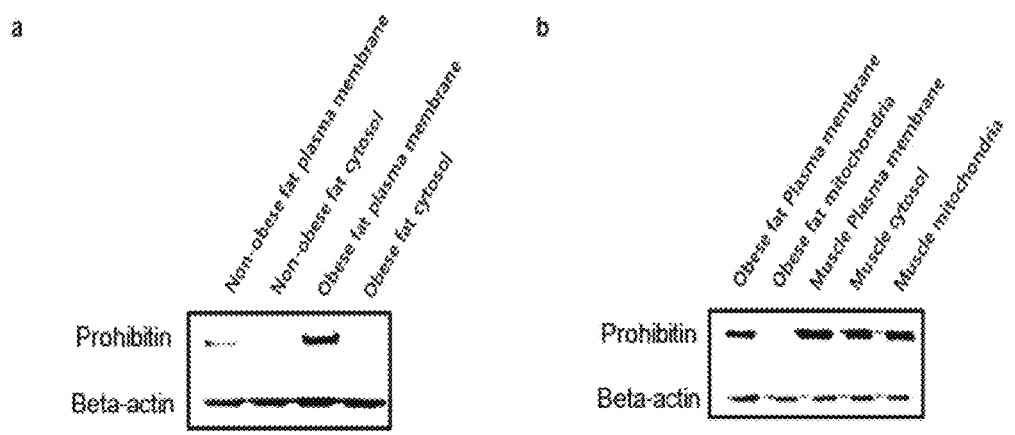

[Fig. 7]
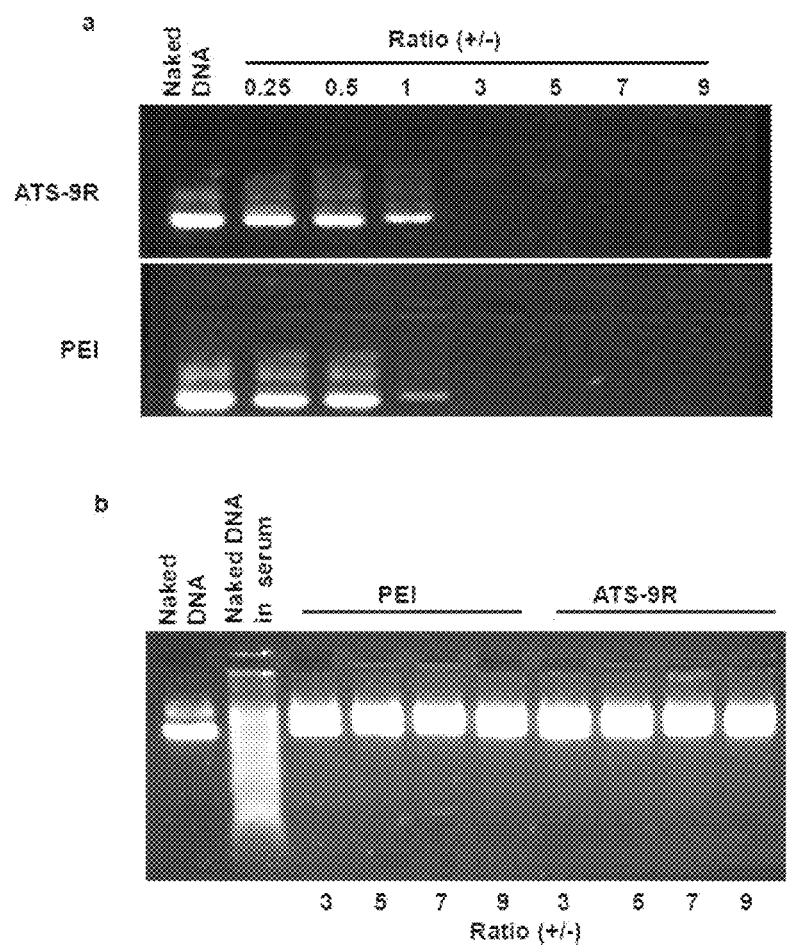

[Fig. 8]
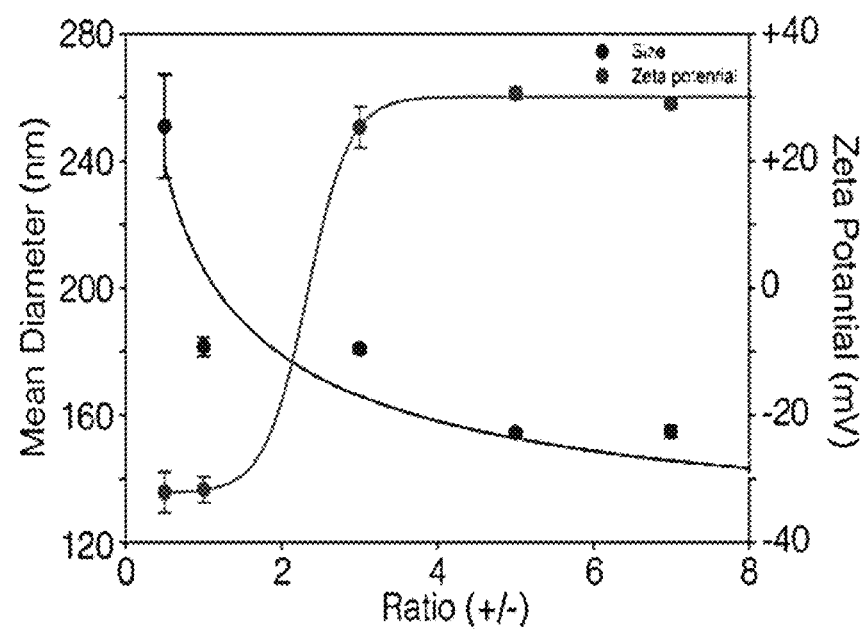

[Fig. 9]
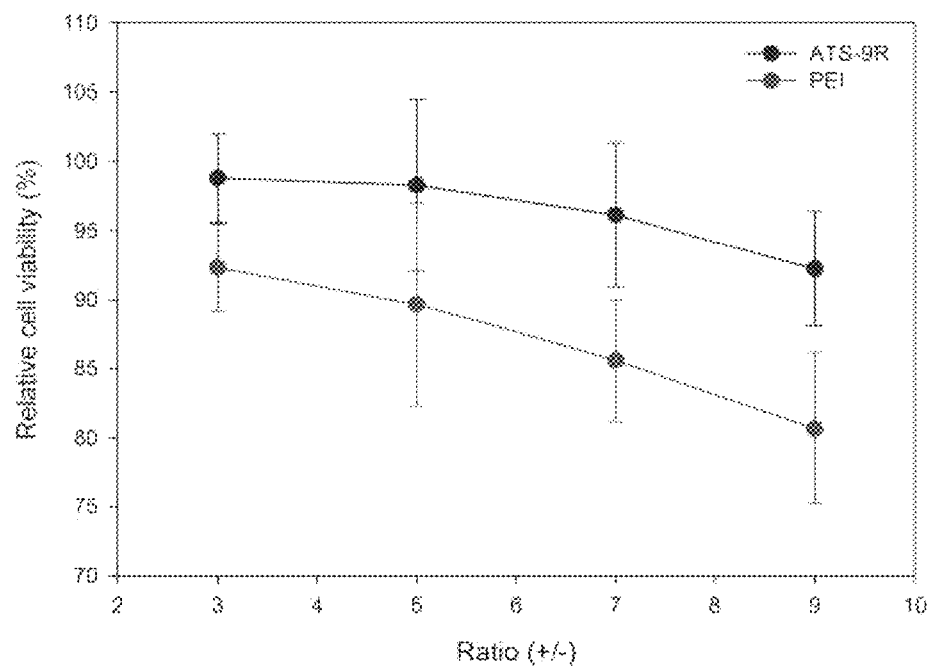

[Fig. 10]
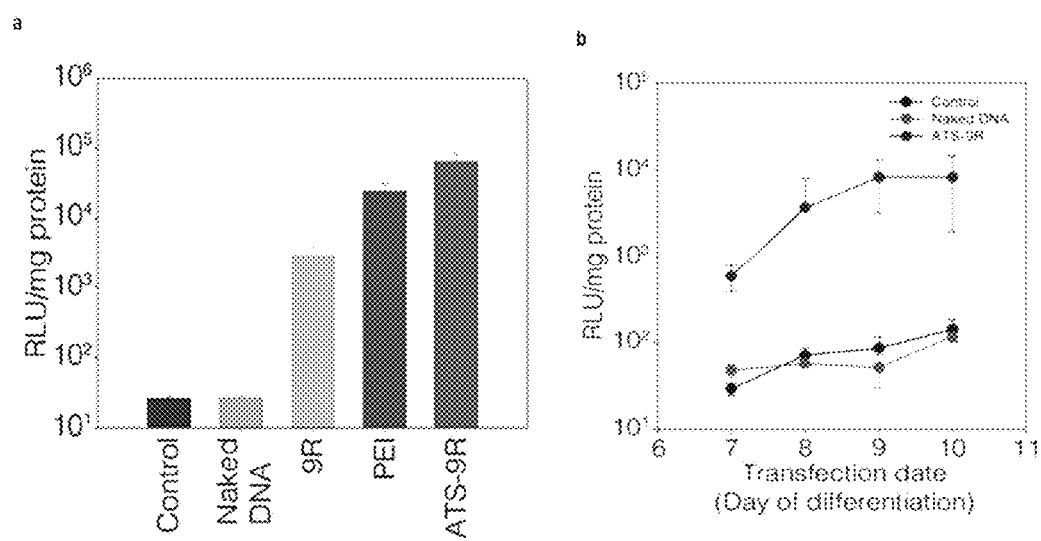

[Fig. 11]
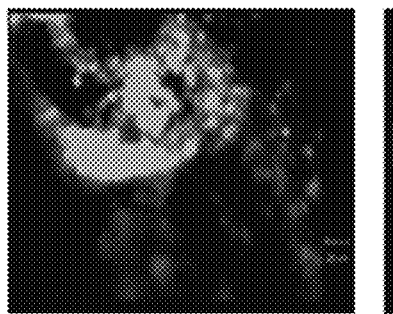 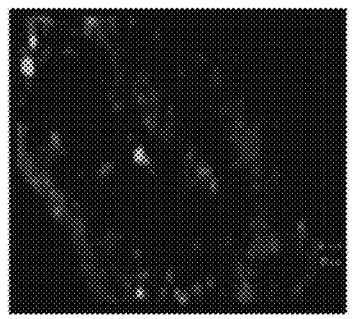 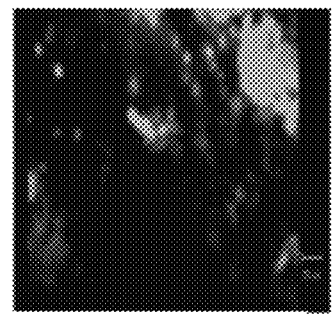
Right abdominal fat pad  Left abdominal fat pad  Gonadal fat pad
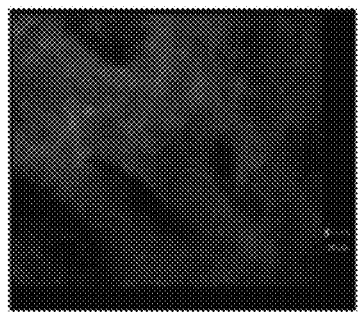 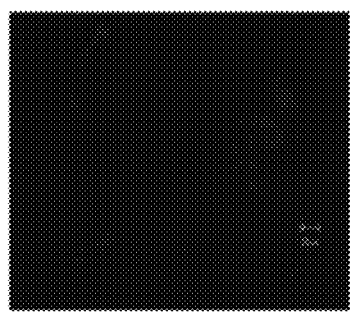
Liver  Kidney

[Fig. 12]
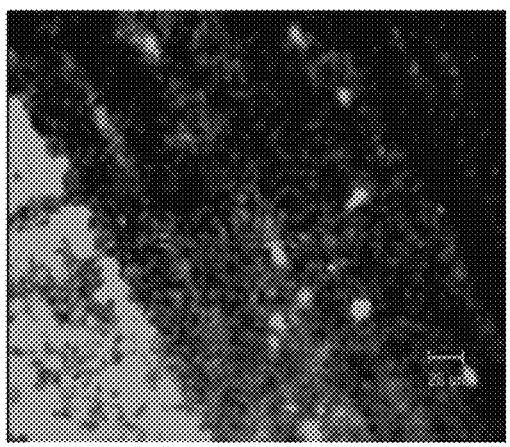 
FITC-ATS-9R      FITC-9R
Left abdominal fat pad vasculature      Left abdominal fat pad vasculature

[Fig. 13]
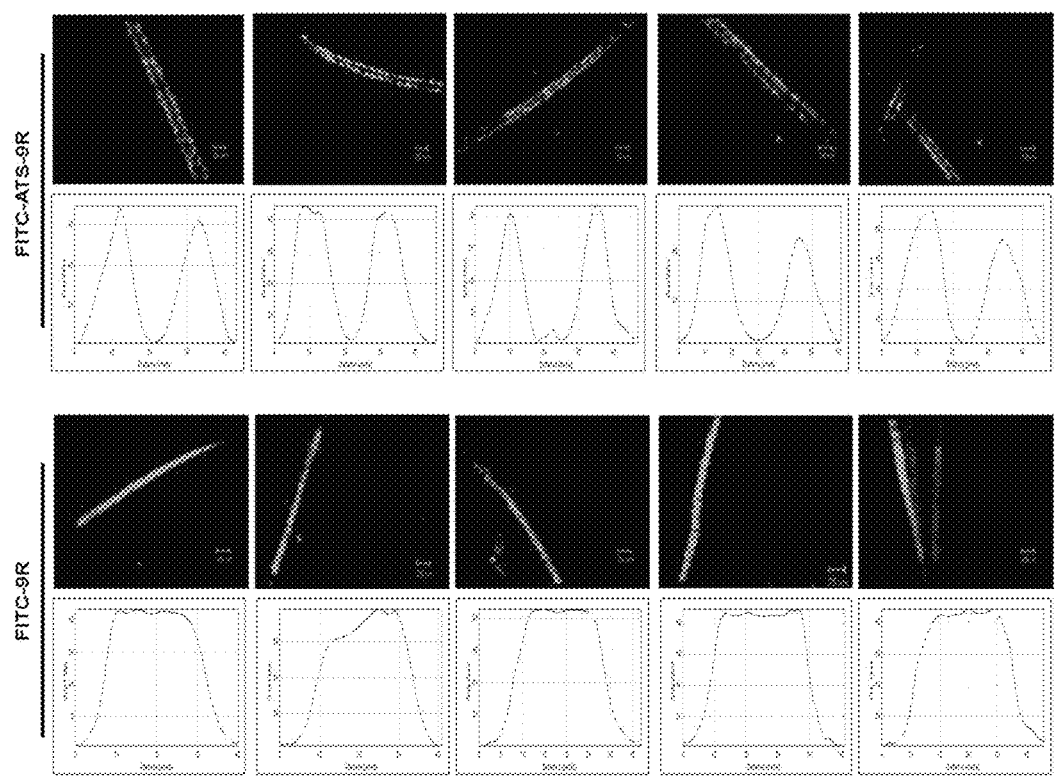

[Fig. 14]
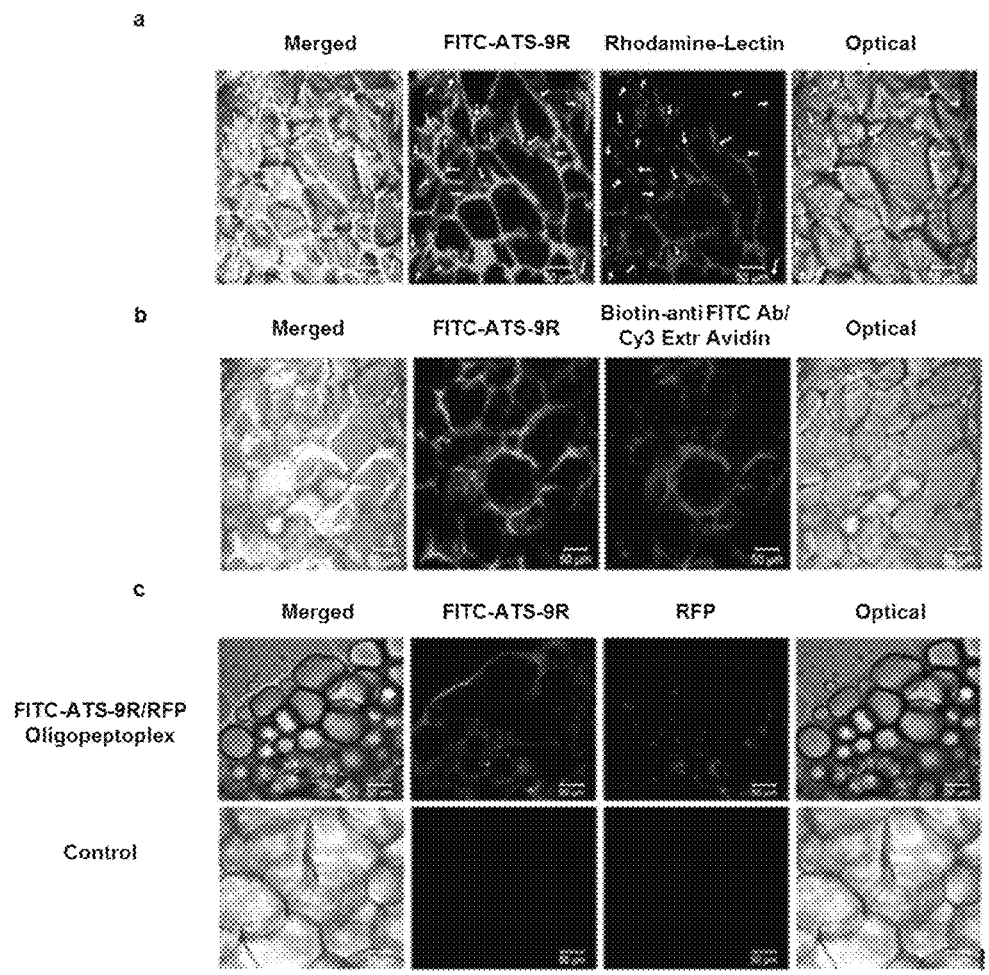

[Fig. 15]
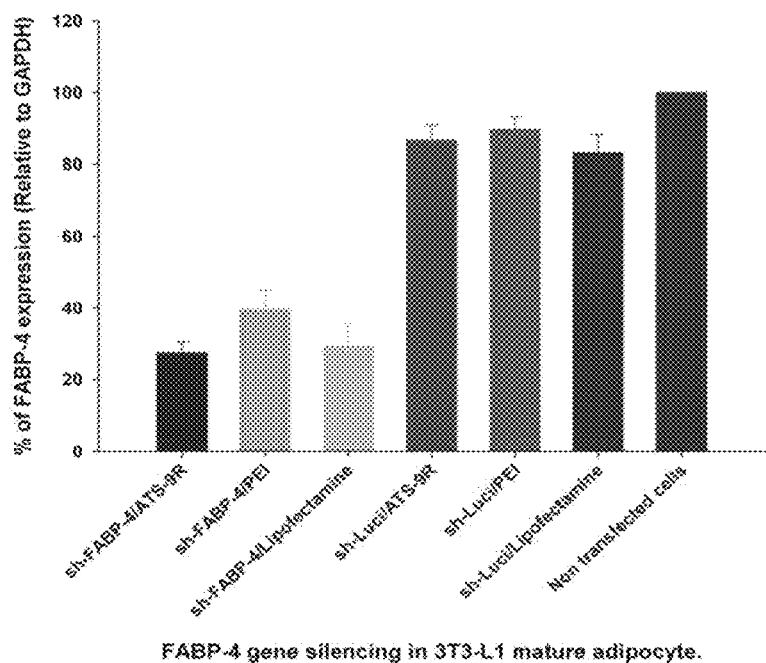

[Fig. 16]
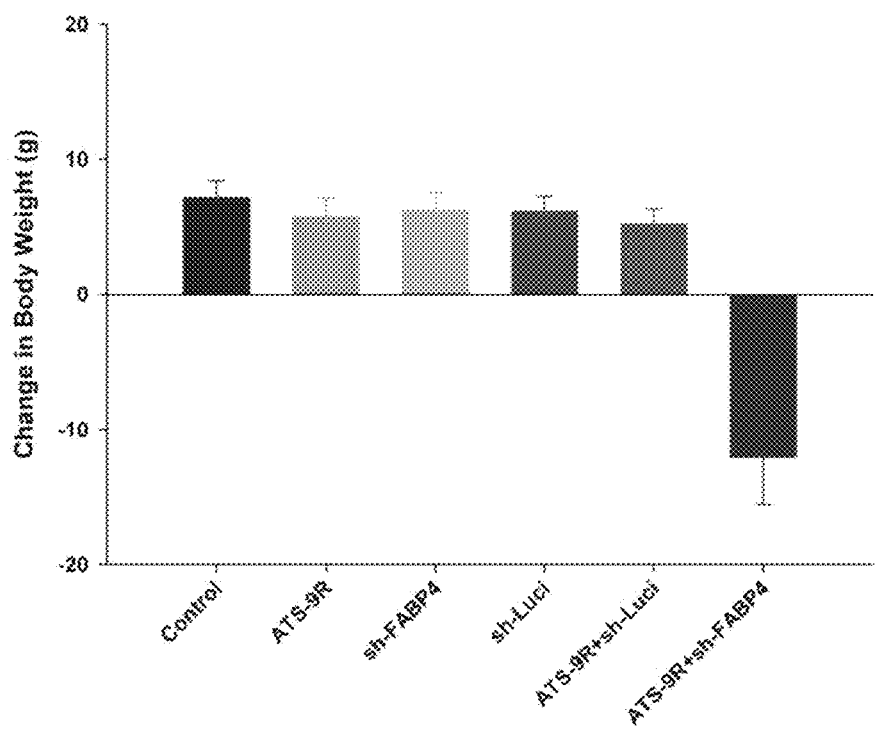

[Fig. 17]
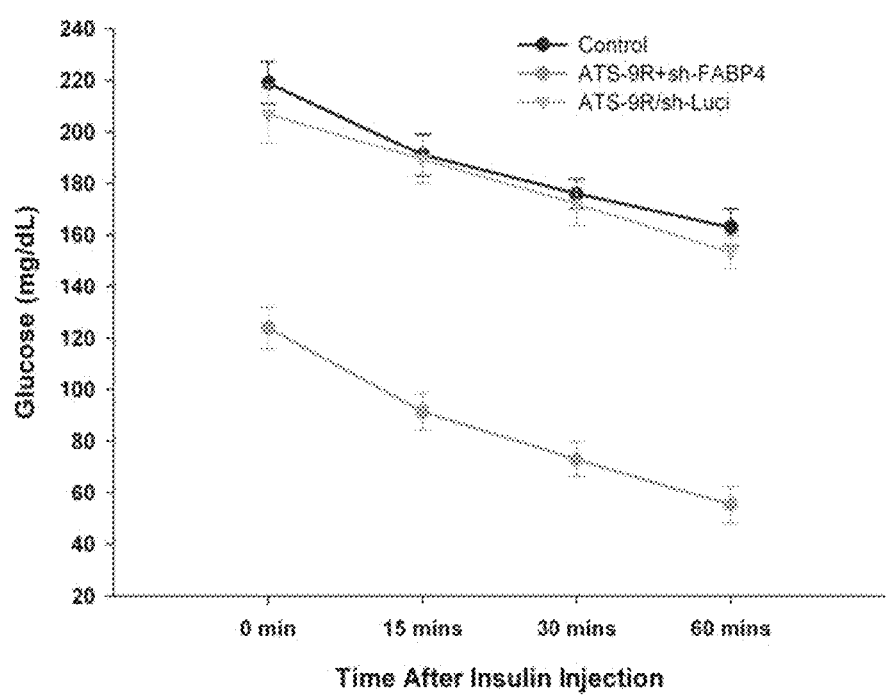

[Fig. 18]
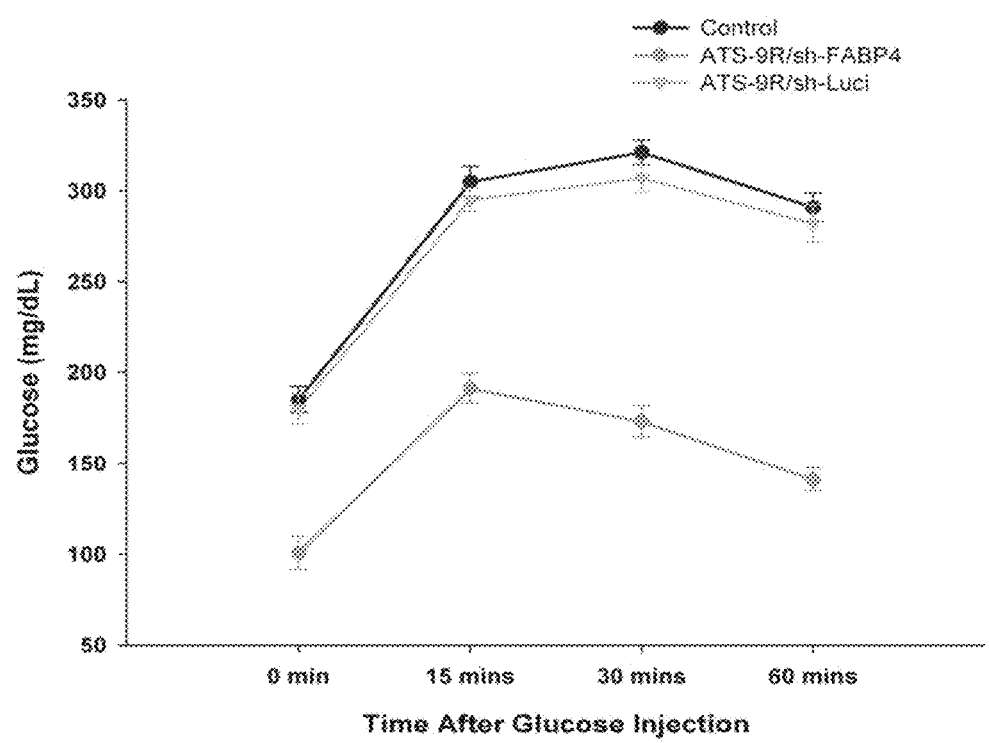

[Fig. 19]
a
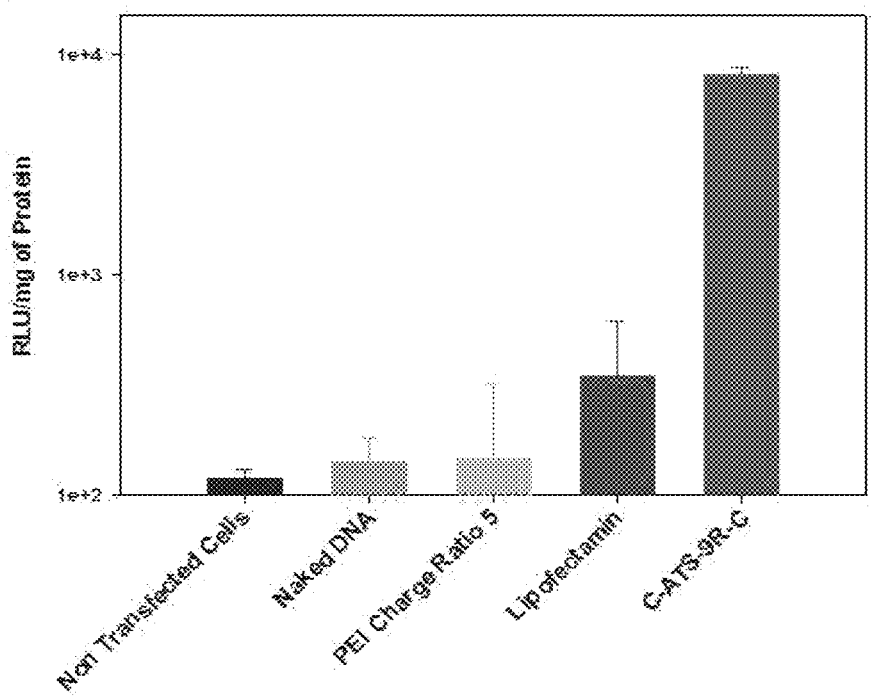
b
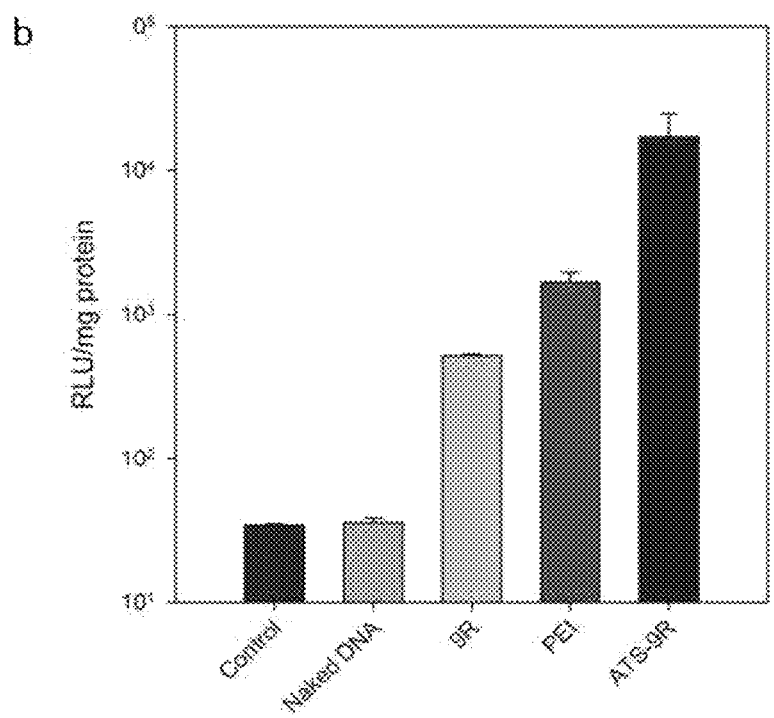

[Fig. 20]
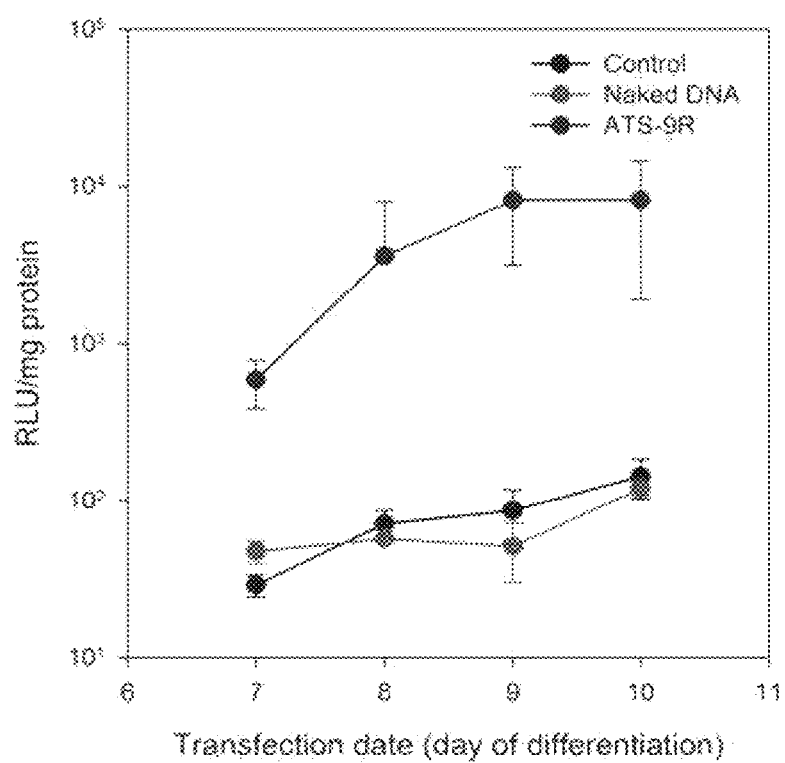

[Fig. 21]
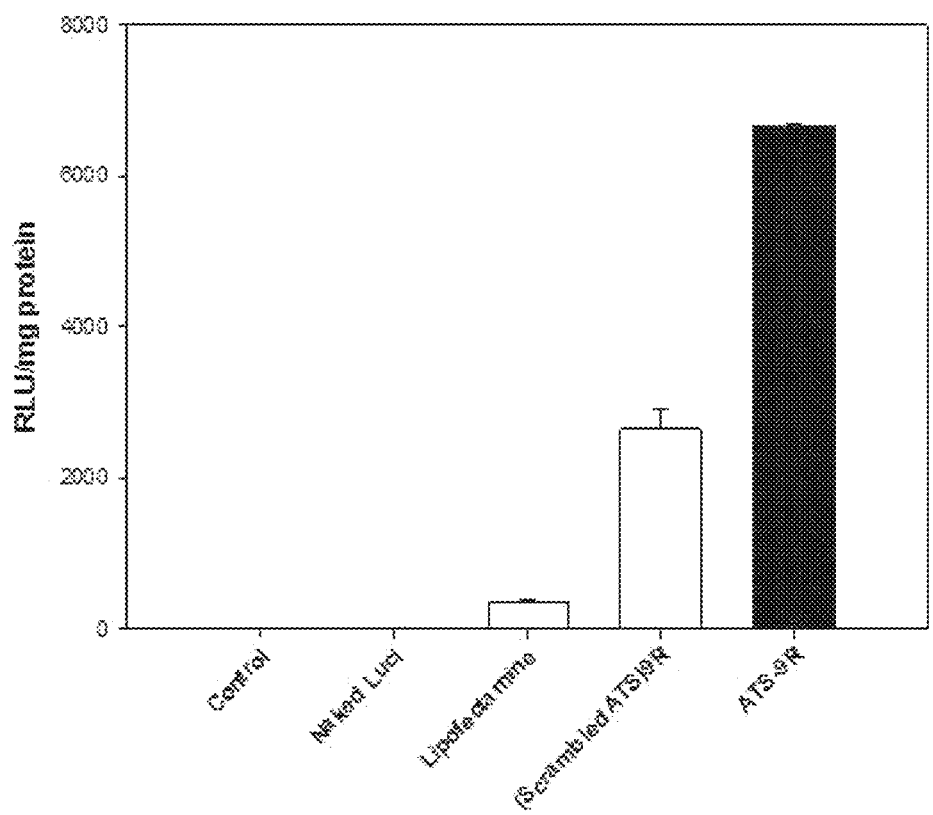

ADIPOCYTE-TARGETING NON-VIRAL GENE DELIVERY SYSTEM

TECHNICAL FIELD

The present invention relates to an adipocyte-targeting non-viral gene delivery system and a therapeutic system for the treatment of obesity and obesity-induced metabolic syndromes using the gene delivery system. More specifically, the present invention relates to a non-viral gene delivery system including an adipocyte-targeting sequence (ATS) and a nona-arginine (R9) peptide wherein the gene delivery system directly targets differentiated obese (mature) adipocytes.

BACKGROUND ART

Various gene therapy approaches have been developed as alternatives to traditional protein therapy approaches. However, important challenges still remain in gene therapy. One of the major challenges of gene therapy is to achieve efficient influx of genes across plasma membranes (in animal cells) and nuclear membranes with minimal cytotoxicity.

Gene therapy systems can be broadly classified into viral vector-mediated systems and nonviral vector-mediated systems. Viral vectors are constructed using retroviruses or adenoviruses and have the advantage of high transfection efficiency into cells. However, viral vectors have problems associated with in vivo immunogenicity and suffer from inherent problems associated with genetic recombination. In attempts to overcome the stability problems of such viral vectors, various polymeric gene delivery systems have been developed as alternatives to traditional viral vector-based gene delivery strategies. For efficient gene delivery, polymeric vectors need to overcome intracellular trafficking barriers, such as endosomal escape and nuclear localization.

On the other hand, gene leakage occurs from synthetic peptide-based gene delivery systems in endosomal membranes at low pH, leading to DNA condensation and rapid endosomal escape. Accordingly, the use of synthetic peptide-based gene delivery systems can overcome the problems encountered with polymeric gene delivery systems. For such reasons, a variety of synthetic peptides have been developed to promote in vitro gene delivery in several cell lines. However, these synthetic peptides also suffer from the problems of toxicity and serum instability in in vivo applications.

As mentioned above, viral vectors have problems in immune response, self-replication, and in vivo stability and general polymeric vectors have the problems of high cytotoxicity and biotoxicity and low nucleic acid delivery efficiency due to their poor biocompatibility.

In this regard, research is being conducted on vectors using short cationic peptides. Even in this case, there are some problems, such as unstable DNA in extracellular spaces. Other problems of the vectors are poor stability of complexes with DNA and low gene expression level.

Under these circumstances, there is a need to develop a gene delivery vector specific for particular cells that possesses the ability to target particular cells and facilitates the influx of DNA into the target cells and the liberation of the DNA from a complex, achieving high expression level of the desired gene.

In this connection, adipocytes, particularly mature obese adipocytes, are final differentiated cells and are thus very difficult to transfect. In previous studies, electroporation has been used to transfect adipocytes but the transfection efficiency was reported to be only about 10%. Moreover, in in vivo gene delivery systems, this method has not been attempted to selectively deliver genes to target adipose tissues.

Thus, the present inventors have investigated non-viral gene delivery systems, and as a result, found for the first time a mechanism in which a peptide complex consisting of a particular peptide and an adipocyte-targeting sequence (ATS) binds to prohibitin expressed in mature adipocytes, directly targets obese adipocytes, delivers genes into the adipocytes, and promotes the expression of the genes, thus being suitable for the treatment of obesity and obesity-induced metabolic syndromes. The present invention has been accomplished based on this finding.

DETAILED DESCRIPTION OF THE INVENTION

Problems to be Solved by the Invention

A principal object of the present invention is to provide an adipocyte-targeting gene delivery system and a complex in which a desired gene is bound to the gene delivery system.

A further object of the present invention is to deliver a therapeutic gene for the treatment of obesity and obesity-induced metabolic syndromes using the gene delivery system.

Another object of the present invention is to provide a pharmaceutical composition for the prophylaxis or treatment of obesity and obesity-induced metabolic syndromes.

Means for Solving the Problems

One aspect of the present invention provides an adipocyte-targeting gene delivery system containing an adipocyte-targeting sequence (ATS) and a nona-arginine (R9) (SEQ ID NO: 4) peptide.

The adipocyte-targeting sequence and the nona-arginine (R9) peptide bind to prohibitin and are internalized into adipocytes.

Particularly, the nona-arginine (R9) peptide preferably has a Cys-(D-R)9-Cys structure (SEQ ID NO: 3) and the adipocyte-targeting sequence may consist of the amino acid sequence set forth in SEQ ID NO: 1.

The adipocytes are preferably differentiated mature obese adipocytes, particularly mature obese adipocytes at 9 to 11 days after initiation of differentiation.

The present invention also provides a complex containing an adipocyte-targeting sequence, a nona-arginine (R9) peptide, and an adipocyte-targeting therapeutic gene for the treatment of obesity and obesity-induced metabolic syndromes.

Specifically, the complex has a structure in which a therapeutic gene, for example, DNA, siRNA or shRNA, for the treatment of obesity and obesity-induced metabolic syndromes is bound to the gene delivery system. The constitution of the gene delivery system is the same as that explained above. The therapeutic gene for obesity treatment is most preferably RNAi (RNA interference gene), such as siRNA or shRNA.

The complex of the therapeutic gene for the treatment of obesity and obesity-induced metabolic syndromes has a diameter of 200 nm or less. Particularly, the nano-sized complex has a charge ratio (+/−) of 3:1 to 8:1. Within this range, high transfection efficiency is ensured. More preferably, the complex has a charge ratio (+/−) of 5:1 to 8:1. High delivery efficiency is obtained when the gene delivery complex is positively charged as a whole because cell membranes are negatively charged. The positively charged complex can easily pass through cell membranes by charge-to-charge interaction. If the complex is negatively charged, it does not readily cross cell membranes. The quantity of electric charges of the complex affects the ability of the complex to cross cell membranes. A larger quantity of electric charges indicates a better ability to cross cell membranes.

The present invention also provides a therapeutic composition for the treatment of obesity and obesity-induced metabolic syndromes containing an adipocyte-targeting sequence, a nano-arginine (R9) peptide, and, as an active ingredient, an adipocyte-targeting therapeutic gene for the treatment of obesity and obesity-induced metabolic syndromes. The therapeutic gene for the treatment of obesity and obesity-induced metabolic syndromes may be DNA or RNAi, such as siRNA or shRNA.

The ATS-R9 of the present invention binds to prohibitin in the adipose tissue vasculature and is subsequently internalized into adipocytes. Briefly explaining, the ATS-R9 of the present invention targets and binds to mature adipose tissue vasculature through prohibitin, passes through the vasculature, and is internalized into adipocytes. Therefore, the ATS-R9 of the present invention specifically targets adipocytes, particularly differentiated mature obese adipocytes in which prohibitin is abundantly expressed, so that it can deliver a desired gene to the adipocytes.

The adipocyte-targeting non-viral gene delivery system of the present invention has high transfection efficiency, low cytotoxicity, and high expression efficiency of a desired gene. Due to these advantages, the gene delivery system of the present invention is effective in the delivery of a desired gene.

Effects of the Invention

The ATS-R9 peptide structure of the present invention directly targets mature obese adipocytes through the mechanism of overexpression of prohibitin in adipocytes after differentiation to deliver a gene to the adipocytes. Due to this specific function and effect, the ATS-R9 peptide structure of the present invention would be very useful in gene therapy for obesity.

BRIEF DESCRIPTION OF THE DRAWINGS

FIG. 1 is a schematic diagram showing the mechanism of targeted gene delivery to adipocytes by ATS-R9 oligo-peptoplexes of the present invention.

FIG. 2 shows the results of Oil Red O staining and quantitative analysis for 3T3-L1 adipocytes according to the degree of adipocyte differentiation.

FIGS. 3 and 4 show the time-dependent intracellular distribution (internalization) of ATS-R9 to demonstrate a specific binding affinity of the ATS-R9 for adipocytes.

FIG. 5 shows the distribution of prohibitin according to the degree of 3T3-L1 adipocyte differentiation.

FIG. 6 compares the expression of prohibitin in non-obese mice and myocytes with that in obese mice, as determined by Western blotting.

FIG. 7 shows the results of gel retardation assay for the ability of ATS-R9 to condense and protect DNA and testing for DNA degradation in mouse serum.

FIG. 8 shows the zeta potentials and mean diameters of ATS-R9/DNA oligo-peptoplexes.

FIG. 9 shows the results of cell viability analysis to evaluate the toxicity of ATS-R9/DNA oligo-peptoplexes.

FIG. 10 shows the transfection efficiency of oligo-peptoplexes.

FIG. 11 shows the targeting effect of ATS-R9 to adipose tissues using diet-induced obesity (DIO) mice.

FIGS. 12 and 13 compare the in vivo homing ability of ATS-R9 with that of R9.

FIG. 14 shows the in vivo gene expression effect of ATS-R9.

FIG. 15 shows the ability of ATS-R9 to in vitro and in vivo deliver sh-RNA and silent gene.

FIG. 16 shows a reduction in body weight after treatment with sh-FABP4-ATS-R9 oligo-peptoplexes.

FIGS. 17 and 18 show changes in insulin and glucose tolerance after treatment with sh-FABP4-ATS-R9 oligo-peptoplexes.

FIG. 19 shows graphs comparing the ability of ATS-R9 to deliver a gene with those of PEI and lipofectamine as controls.

FIG. 20 is a graph comparing the gene delivery efficacies of ATS-R9 before and after adipocyte differentiation.

FIG. 21 is a graph comparing use of the gene delivery efficacies of ATS-R9 before and after adipocyte differentiation.

BEST MODE FOR CARRYING OUT THE INVENTION

The definitions of the terms used herein are as follows.

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

The term "polynucleotide" or "nucleic acid" refers to a polymeric form of nucleotides of any length, such as deoxyribonucleotides as well as ribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications, such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The term "vector" refers to a nucleic acid molecule capable of transporting another nucleic acid to which it has been linked. The term "expression vector" is intended to include a plasmid, cosmid or phage, which can synthesize Neuritin (CPG15) encoded by a recombinant gene carried by the vector. A preferred vector is a vector that can self-replicate and express a nucleic acid bound thereto.

By "transfection" is meant a process by which a nucleic acid (e.g., DNA or RNA) is directly introduced into an animal culture cell to express its genetic traits. When targets are plant cells, the cell walls are removed and nucleic acids are introduced into protoplasts in many cases. This process enables access to many issues in medical science and biology, such as carcinogenic mechanism, infection, immunity, genesis, and information delivery, in a cellular level. Generally, a desired gene is contained in a carrier, such as a plasmid, and introduced into the nucleic acid. In many cases, the introduced gene is inserted into a chromosome when stabilized in the cell. The cell into which the nucleic acid has been introduced is called a "transductant". Several processes have been developed to overcome the problem of low transduction efficiency. Examples of such processes include calcium phosphate co-precipitation, DEAE-dextran treatment, electroporation, and redistribution (fusion of artificial membranes called liposomes with cells for DNA complexation).

By "zeta potential" is meant the electrokinetic potential arising from a density gradient of positive charges in a diffuse double layer of immobile water attached to the surface of a charged particle and mobile water easily detachable from the particle. Zeta potential is also expressed as an electrical potential difference between cell surface and surrounding culture fluid.

By the term "charge ratio" in a complex that functions as a gene delivery system, it is meant the ratio of the quantity of charges of a support or carrier to that of charges of DNA when the negatively charged DNA is bound to the positively charged support or carrier by an electrostatic attractive force. When the complex is positively charged as a whole, good delivery efficiency is attained, which is explained by the fact that the cell membrane is negatively charged.

The terms "amino acid" and "amino acid residue" are intended to include natural amino acids, non-natural amino acids, and modified amino acids. Unless otherwise stated, all mentions about amino acids include general mentions about the amino acids and specific mentions about both D- and L-stereoisomers of the amino acids (so long as their structures allow such stereoisomeric forms) according to their names. Examples of the natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). The non-natural amino acids include modified amino acid residues which are chemically modified, reversibly or irreversibly, or chemically blocked on their N-terminal amino group or their side chain groups, for example, N-methylated D and L amino acids or residues whose side chain functional groups are chemically modified to other functional groups.

The term "progenitor cell" refers to an undifferentiated cell with self-renewal ability and differentiation potency but is a cell that is to be ultimately differentiated into a predetermined type of cell. The progenitor cell is committed to a differentiation pathway and generally does not express markers or function as a mature fully differentiated cell. Accordingly, the progenitor cell is differentiated into relevant cell types but can form a wide variety of cell types in the normal state. In the present invention, preadipocytes are used that are to be differentiated into adipocytes.

The term "differentiation" refers to a phenomenon in which the structure or function of cells is specialized during the division, proliferation, and growth thereof, that is, the feature or function of cell or tissue of an organism changes in order to perform work given to the cell or tissue. In the present invention, this term is used to describe differentiated mature adipocytes.

"Luciferase" is an enzyme that catalyzes the oxidation of luciferin to convert chemical energy into light energy, achieving light emission. Luciferase functions like a reporter gene whose in vivo expression is continuously measured in real time and whose effect on a target material can be verified. Luciferase is obtainable directly from the bodies of insects such as fireflies or glow-worms. Alternatively, luciferase may be obtained by expression in a microorganism including a recombinant DNA fragment encoding the enzyme.

The term "support or carrier" refers collectively to polymeric materials responsible for carrier transport when active materials are present in a bound form with other materials in organisms or materials migrate through cell membranes. Non-limiting examples of supports suitable for use in the present invention include: buffers, such as phosphate, citrate, and other organic acids; antioxidants, such as ascorbic acid; low molecular weight (less than about 10 residues) polypeptides; proteins, such as serum albumin, gelatin or immunoglobulins; hydrophilic polymers, such as polyvinylpyrrolidone; amino acids, such as glycine, glutamine, asparagine, arginine or lysine; other carbohydrates, such as monosaccharides, disaccharides, glucose, mannose, and dextrins; chelating agents, such as EDTA; sugar alcohols, such as mannitol and sorbitol; salt-forming counterions, such as sodium; and/or nonionic surfactants, such as TWEEN®, polyethylene glycol (PEG), and PLURONICS®.

The term "treatment" is an approach to obtain beneficial or desired results, including clinical results. "Treatment" or "alleviation" of a disease, a disorder or a condition means that the extent of the condition, disorder or disease and/or undesired clinical symptoms is reduced and/or the progression of the condition, disorder or disease is retarded or prolonged, compared to when the condition, disorder or disease is not treated. In the treatment of obesity, for example, a desired result may be a reduction in weight body, for example, a weight loss of at least 5%. For the purposes of the present invention, beneficial or desired results can include, but are not limited to, relief or amelioration of one or more symptoms, diminishment of extent of disease, stabilized (i.e. not worsening) state of disease, delay or slowing of disease progression, amelioration or alleviation of disease state, and remission (whether partial or total), whether detectable or undetectable. "Treatment" can also mean prolonged survival compared to expected survival when no treatment is received. "Treatment" is not necessarily limited by administration of a single dose and is often effected by administration of a series of doses. Thus, a therapeutically effective amount, an amount sufficient to alleviate or an amount sufficient to treat a disease, disorder or condition can be administered once or more.

The term "disorder" is any condition that would benefit from treatment with molecules identified using a transgenic animal model. This includes chronic and acute diseases or illness including pathological conditions that predispose mammals to diseases in question. Non-limiting examples of diseases to be treated herein include obesity and metabolic syndromes.

By "therapeutically effective amount" is meant the amount of an active compound in a composition that will elicit the biological or medical response (including relief of symptoms of a disorder to be treated) of a tissue, system, subject or human in need thereof that is being sought by a researcher, veterinarian, medical doctor or other clinician.

By "prophylactically effective amount" is meant the amount of an active compound in a composition that will elicit the biological or medical response (including relief of symptoms of a disorder to be treated) of a tissue, system, subject or human in need thereof that is being sought by a researcher, veterinarian, medical doctor or other clinician, to prevent the onset of obesity or an obesity-induced disorder, condition or disease in subjects as risk for obesity or the obesity-induced disorder, condition or disease.

The term "gene therapy" refers to the treatment of a genetic disease by modifying a mutated gene or the treatment of a disease by regulating protein expression using a gene or RNAi. That is, gene therapy is a process for the treatment of a disease by transplanting an exogenous normal gene into the cell of a patient to change the phenotype of the cell. Ethical issues of gene therapies for human sperms, ova, and embryos are currently controversial around the world. Since the establishment of "Guidelines for Gene Therapy Clinical Research" in 1993, the era of gene therapy has begun. Research on gene vectors and systems for in vivo gene transfection is essential for gene therapy.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "include (comprise)," "includes (comprises)," and "including (comprising)" will be understood to imply the inclusion of a stated step or element or group of steps or elements but not the exclusion of any other step or element or group of steps or elements.

The present invention will now be described in detail.

The present invention is directed to intracellular delivery (transfection) of nucleic acids, and particularly to delivery of adipocyte-targeting therapeutic genes, such as DNA, siRNA, and shRNA, for the treatment of obesity and obesity-induced metabolic syndromes using delivery systems directly targeting adipocytes.

In one aspect, the present invention provides an adipocyte-targeting gene delivery system including an adipocyte-targeting sequence (ATS) and a poly(oligo-arginine), particularly a nona-arginine (R9) peptide. Specifically, the present invention provides a non-viral gene delivery vector including an adipocyte-targeting sequence (ATS) and a reducible poly(oligo-arginine).

The non-viral gene delivery vector refers collectively to carriers that transfer genes into cells without using viruses. Representative examples of such non-viral gene delivery vectors are vectors that coat nucleic acids based on the electrical interaction between cationic sites on the vectors and anionic sites on the negatively charged nucleic acids constituting genes.

The poly(oligo-arginine) includes a poly(oligo-L-arginine) and a poly(oligo-D-arginine), most preferably a poly(oligo-D-arginine). A high molecular weight poly(oligo-D-arginine) effectively promotes the condensation of DNA to form a stable complex and internalizes the DNA into a cell. After internalization, the complex escapes from an endosome to the cytoplasmic space by the reduction of disulfide bonds.

The reducible poly(oligo-D-arginine) preferably consists of cationic oligomers, each of which includes cysteine residues cross-linked by a disulfide bond at the terminal positions, but is not limited thereto. Cysteine is the only amino acid that contains a sulfhydryl group capable of cross-linking with an adjacent cysteine molecule to form a disulfide. The protein transduction domain (PTD) portions other than the cysteine residues cross-linked by disulfide bonds may become any cationic peptides. For example, the reducible poly(oligo-D-arginine) may consist of Cys-(D-R)9-Cys repeating units. The reducible poly(oligo-D-arginine) may be prepared by DMSO oxidation of the terminal cysteine-thiol groups of the Cys-(D-R)9-Cys repeating units. The reducible poly(oligo-D-arginine) may be cleaved into Cys-(D-R)9-Cys fragments by treatment with a reducing agent.

That is, the reducible poly(oligo-arginine) may consist of nine arginine residues. Preferably, the reducible poly(oligo-arginine) has a Cys-(D-R)9-Cys structure. The presence of Cys residues at both terminal positions enables effective condensation of an oligo-peptide complex (peptoplex) and allows the resulting complex to have neutral charge characteristics.

The gene delivery system of the present invention includes a nona-arginine (R9) peptide and an adipocyte-targeting sequence (ATS). Specifically, the gene delivery system of the present invention includes a structure in which the nona-arginine (R9) peptide is bound to the adipocyte-targeting sequence (ATS) (ATS-R9).

The adipocyte-targeting sequence (ATS) may be any of those known in the art. For example, the adipocyte-targeting sequence (ATS) may be found in Nature medicine, 2004 June. Preferably, the adipocyte-targeting sequence (ATS) consists of the amino acid sequence set forth in SEQ ID NO: 1:

SEQ ID NO: 1: CKGGRAKDC

The ATS-R9 of the present invention binds specifically to prohibitin in adipocytes.

Prohibitin is an ATS receptor that is overexpressed in adipocyte-supporting vascular endothelial cells and is present in both mature adipocytes and preadipocytes. Therefore, the expression location and level of prohibitin can be confirmed by determining the ability of prohibitin to bind to the ATS instead of the antibody thereof.

Particularly, prohibitin plays an important role in obesity. Prohibitin is highly expressed in adipose tissue blood vessels and tends to migrate from the nuclei and mitochondria to the plasma membranes of adipocytes after differentiation compared to before differentiation. This feature suggests that prohibitin may be a potential biomarker for obesity. Prohibitin is less distributed in the plasma membranes of preadipocytes and is more abundantly located in the nuclei and mitochondria thereof. However, prohibitin located in the nuclei and mitochondria of differentiated adipocytes migrates to and is highly expressed in the plasma membranes. That is, prohibitin is overexpressed as the differentiation of adipocytes proceeds.

The ATS-R9 of the present invention is internalized into adipocytes through a prohibitin-mediated mechanism. That is, the ATS plays an important role in adipocyte targeting and the expression level of a desired gene is dependent on the expression level of prohibitin in adipocytes.

Particularly, prohibitin is more overexpressed in mature adipocytes after differentiation than in adipocytes before differentiation. For this reason, the ATS-R9 of the present invention has the function of directly targeting differentiated mature obese adipocytes, which can be confirmed in Experimental Example 1. The ATS-R9 of the present invention has the best ability to target mature obese adipocytes, particularly those at 9 to 11 days after initiation of differentiation. The terms "mature adipocytes" and "obese adipocytes" have the same meaning and are used interchangeably herein.

Thus, the present invention is directed to a method and related system for efficiently delivering a specific gene to adipocytes by using the gene delivery system targeting obese adipocytes. The specific gene targeting obese adipocytes may be a known therapeutic gene for the treatment of obesity and obesity-induced metabolic syndromes.

In a further aspect, the present invention provides a complex containing an adipocyte-targeting sequence (ATS), a nona-arginine (R9) peptide, and an adipocyte-targeting therapeutic gene for the treatment of obesity and obesity-induced metabolic syndromes wherein the desired gene is bound to the gene delivery system.

The target cells may also be cells corresponding to preadipocytes capable of differentiating into adipocytes but are most preferably mature adipocytes (e.g., obese adipocytes, white adipocytes, and brown adipocytes).

The preadipocytes include mesenchymal stem cells and stromal cells whose differentiation potency into various kinds of cells, including adipocytes, is maintained, as well as cells capable of directly differentiating into adipocytes. These cells may also be primary culture cells from adipose tissues of humans or non-human mammals. The cells may also be established cultured cell lines.

Examples of suitable sources of the adipose tissues include subcutaneous fat and visceral fat but are not limited thereto. The adipose tissues that cause less risk of damage to the functions of individuals after collection are very suitable as sources of the target cells. The mesenchymal stem cells and stromal cells may be collected from bone marrow and other tissues.

The therapeutic gene for the treatment of obesity and obesity-induced metabolic syndromes to be delivered by the complex of the present invention may be any suitable gene that is expressed in target adipocytes, and examples thereof includes DNA, RNA, and their synthetic analogues. Suitable genes include genes encoding polypeptides (enzymes, hormones, growth factors, cytokines, receptors, structural proteins, etc.), antisense RNAs, ribozymes, decoys, and RNAs that cause RNA interference, and specific examples thereof include gDNA, cDNA, pDNA, mRNA, tRNA, rRNA, siRNA, miRNA, and antagomirs. They may be naturally occurring or artificially synthesized and may have various sizes from oligonucleotides to chromosomes. These genes may be derived from humans, animals, plants, bacteria, viruses, etc. and may be acquired by known methods known in the art.

The polypeptides encoded by the genes may include various hormones, histocompatible antigens, cell adhesion proteins, cytokines, various antibodies, cell receptors, endoenzymes, ectoenzymes, and fragments thereof. The complex of the present invention may include gene expression regulatory factors for the treatment of obesity and obesity-induced metabolic syndromes, for example, transcription promoters, enhancers, silencers, operators, terminators, attenuators, and other expression regulatory factors.

Preferably, the therapeutic gene for the treatment of obesity and obesity-induced metabolic syndromes includes genes encoding polypeptides associated with the treatment or diagnosis of obesity and obesity-induced metabolic syndromes. The therapeutic gene for the treatment of obesity and obesity-induced metabolic syndromes is particularly preferably RNAi that is effective in gene therapy for obesity diseases.

RNA interference is a natural mechanism including specifically downregulating the expression of desired genes by double-stranded short interfering RNA (siRNA). Various types of RNAi-mediating agents are known and examples thereof include short interfering RNA (siRNA), microRNA (miRNA), and small hairpin RNA (shRNA).

Thus, in another aspect, the present invention provides a composition for the treatment of obesity or obesity-induced metabolic syndromes including a complex containing an adipocyte-targeting sequence (ATS), a nona-arginine (R9) peptide, and an adipocyte-targeting therapeutic gene for the treatment of obesity and obesity-induced metabolic syndromes.

As explained previously, the therapeutic gene for the treatment of obesity and obesity-induced metabolic syndromes is preferably a gene that is effective in gene therapy for obesity diseases, for example, RNAi.

Effective doses and dosage regimes for the administration of the RNAi can be empirically determined by those skilled in the art. The RNAi can be administered in either single or multiple doses.

On the other hand, the term "obesity or obesity-induced metabolic syndromes" used herein is generally defined as having a body mass index (BMI) exceeding 30. For the purposes of the present invention, all targets who need or want to prevent further weight gain, including those who have a BMI of less than 30, fall within the category of "obesity".

The gene exists in the form of a negatively charged giant polymer chain. Accordingly, when the gene exists alone, it takes the form of a relatively bulky random coil. This form makes the gene difficult to deliver to cells. Thus, it is necessary to reduce the gene to smaller nanoparticles. In the present invention, the size of the complex is reduced to the nanometer range based on electrostatic interaction of the ATS-R9 with the gene. The term "biodegradable bond" used herein refers to a bond that is cleaved to convert a material into a less complex intermediate or end product by solubilization hydrolysis or by the action of an enzyme, an organism, etc. Particularly, when the disulfide-bonded ATS-R9 of the present invention enters adipocytes, it is cleaved into lower molecular weight molecules, and as a result, the desired gene can be liberated from the complex.

The delivery system and the complex for the delivery of the substance to adipocytes according to the present invention have the following advantages.

(1) The ATS in the ATS-R9 of the present invention plays an important role in adipocyte targeting.

The ATS-R9 delivery system of the present invention targets adipose tissue endothelial cells through binding to prohibitin expressed in adipocytes. That is, the ATS targets adipocytes and is internalized into the adipocytes through a prohibitin-mediated mechanism. Particularly, the target cells are most preferably differentiated mature obese cells in which prohibitin is overexpressed.

In the Examples section that follows, pretreatment with free ATS was confirmed to reduce luciferase gene expression. This indicates that ATS-R9 oligo-peptoplexes entered cells through binding to prohibitin. The ATS-R9 of the present invention showed higher transfection efficiency and gene expression efficiency than PEI and R9.

For high efficiency of the gene delivery system, the support should be able to pass through nuclear membranes and should deliver the gene cargo to nuclei. Since prohibitin is highly expressed in the nuclei of mature adipocytes, the ATS-R9 should rapidly cross the nuclei. This strongly suggests that the ATS, a prohibitin targeting moiety, is very important in efficient targeting to adipocytes and selective gene expression in adipocytes. That is, prohibitin becomes a potential target for selective transfection of mature adipocytes.

(2) The ATS-R9 of the present invention improves the transgene expression efficiency of the therapeutic gene for the treatment of obesity and obesity-induced metabolic syndromes after delivery.

The gene is easily condensed in the ATS-R9 of the present invention at a charge ratio (+/−) of ≥3:1, preferably 3-8:1, more preferably 5-8:1, achieving high transfection efficiency of the ATS-R9. Particularly, in the Examples section that follows, the delivery system of the present invention showed the highest gene transfection efficiency at a charge ratio of 5:1.

The charge ratio refers to the ratio of the positively charged arginine constituting the delivery system to the negatively charged phosphate groups constituting the gene. In the present invention, the negatively charged gene is allowed to react with a 3- to 8-fold excess of the delivery system. That is, the charge ratio of 3:1 to 8:1 indicates that the amount of the delivery system is 3 to 8 times larger than that of the desired gene.

High delivery efficiency is obtained when the gene delivery complex is positively charged as a whole because cell membranes are negatively charged. The positively charged complex can easily pass through cell membranes by charge-to-charge interaction. If the complex is negatively charged, it does not readily cross cell membranes. The quantity of electric charges of the complex affects the ability of the complex to cross cell membranes. A larger quantity of electric charges indicates a better ability to cross cell membranes.

On the other hand, the degree of adipocyte differentiation may affect the transfection efficiency of the ATS-R9. The transfection efficiency of the ATS-R9 increases gradually until 10 days of differentiation. As the degree of differentiation and the number of differentiated adipocytes increase, prohibitin is upregulated, enhancing the transfection efficiency of the ATS-R9. In the Examples section that follows, the ATS-R9 was confirmed to have the highest transfection efficiency for mature obese adipocytes at 9 to 11 days after initiation of differentiation.

As demonstrated above, the complex of the present invention enables expression of the desired gene depending on the expression level of prohibitin in adipocytes.

Particularly, the ATS-R9 of the present invention has much higher gene expression efficiency than cationic polyethylenimine (PEI) supports generally used in the art. That is, the ATS-R9 exhibits the ability to more effectively condense DNA and protects DNA from degradation in serum at the optimum charge ratio defined above.

(3) The ATS-R9 of the present invention binds to DNA to form the nano-sized complex and has a positive zeta potential value.

When the ATS-R9 is bound to DNA, it more effectively condenses DNA by electrostatic interaction in a relatively low polymer nitrogen (+)/pDNA phosphate (−) (N/P) ratio. That is, the ATS-R9 bears a positive charge under neutral conditions, enabling effective concentration of DNA to a nanometer size (ca. ≤200 nm) and allowing the ATS-R9 to have a positive zeta potential at a charge ratio of ≥1. This is because the oligo-peptide includes Cys residues at both terminal positions.

As explained earlier, the positively charged complex can easily pass through cell membranes by charge-to-charge interaction. If the complex is negatively charged, it does not readily cross negatively charged cell membranes. Accordingly, the positive zeta potential value of the complex suggests high gene delivery efficiency of the complex.

(4) The ATS-R9 of the present invention has low cytotoxicity.

In comparison with a PEI support as a general cationic polymer support, the ATS-R9 of the present invention has low cytotoxicity. In the Examples section that follows, the ATS-R9 showed non-toxicity at charge ratios up to 9 and a cell viability of at least 90% at all charge ratios whereas the PEI support showed toxicity.

To sum up, the ATS-R9 of the present invention binds to prohibitin in adipose tissue blood vessels and is then effectively internalized into adipocytes, particularly differentiated mature obese adipocytes. That is, the in vivo localization of the ATS-R9 can be briefly explained by three steps: targeting and binding to adipose tissue blood vessels through prohibitin; passing through blood vessels; and internalization into adipocytes.

In addition, the gene delivery system of the present invention has high transfection efficiency, low cytotoxicity, and high expression efficiency of a desired gene, thus being suitable for the treatment of obesity and obesity-induced metabolic syndromes.

Mode For Carrying Out The Invention

The present invention will be explained in more detail with reference to the following examples. However, it will be obvious to those skilled in the art that these examples are provided for illustrative purposes only and are not construed as limiting the scope of the invention.

Cell Culture

Dulbecco's Modified Eagle's Medium (DMEM), glucose, and FBS were purchased from WelGENE (Korea), insulin and 3-isobutyl-1-methylxanthine (IBMX) were purchased from Wako (Japan), and Dexamethasone and Oil Red O were purchased from Sigma-Aldrich (U.S.A.). 3T3-L1 preadipocytes were purchased from the Korean cell line bank. The preadipocytes were induced to differentiate.

The preadipocytes were cultured in complete medium supplemented with glucose, 10% FBS, 1% penicillin, and streptomycin at 37° C. in an atmosphere of 5% $CO_2$. The cells were passaged three times a week. For adipocyte differentiation, 4 days after seeding, the cells were treated with a differentiation induction medium containing complete medium, 10 µg/ml insulin, 1 µM Dexamethasone, and 0.5 mM IBMX for 72 h. The differentiation medium was replaced with an adipocyte maintenance medium containing complete medium and 10 µg/ml insulin. Media were changed every two days.

Peptide Preparation

Rhodamine B conjugated ATS (CKGGRAKDC) peptide, (SEQ ID NO: 1), FITC conjugated ATS-R9 (CKGGRAKDRRRRRRRRRC), (SEQ ID NO: 2), and R9 (CRRRRRRRRRC) peptide (SEQ ID NO: 3) were purchased from Peptron (Daejeon, Korea). The peptides were lyophilized, dissolved in deionized water, and stored at −20° C. before use.

The molecular weights of the peptides were as follows: ATS: 937, Rhodamine B ATS: 1361, ATS-R9: 2341, FITC-ATS-R9: 2844, R9: 1628.

Oil Red O Staining

Adipocyte differentiation was confirmed by Oil Red O staining.

For the preparation of Oil Red O solution, 0.7 g of Oil Red O powder was dissolved in 200 ml isopropanol, stirred overnight, and filtered through a 0.22 μm syringe filter. The Oil Red O solution was mixed with deionized water in a ratio of 6:4 to prepare Oil Red O working solution, which was filtered through a 0.22 μm syringe filter.

For cell staining, the cells were rinsed with Phosphate Buffered Saline (PBS) and fixed for 1 h at room temperature with PBS containing 3.7% formaldehyde. After fixation, the cells were washed with 60% isopropanol and dried under a clean bench. After being completely dried, the cells were stained with Oil Red O working solution and incubated for 15 min.

The cells were washed four times with deionized water and images were captured by microscope. For quantitative analysis of adipocyte differentiation, accumulated Oil Red O was eluted from cells by 100% isopropanol and absorbance was taken at 520 nm.

Sample Preparation for Confocal Microscopy

Cellmask Deep Red was purchased from Invitrogen and DAPI-Fluoromount-G was purchased from Southern Biotech. 3T3-L1 preadipocytes, H9c2, and HEK293 cells were grown and differentiated on coverslips placed in 6 well plates.

After 24 h of seeding, the cells were treated with the FITC conjugated ATS-R9 (25 μg/ml) and incubated in a time-dependent manner that ranged from 15 min to 72 h.

After incubation, culture media were replaced, and the cells were washed three times with PBS and fixed in 3.7% formaldehyde. The plasma membranes of the cells were stained with Cellmask Deep Red. The cells were washed again with PBS and mounted in the presence of DAPI to stain the nuclei. Images were captured with a Carl Zeiss confocal microscope.

Competition Assay

For competition assay, 3T3-L1 preadipocytes and mature adipocytes (at day 10) were treated with free ATS (100 μg/ml). After 6 h of culture, the cells were treated with FITC-ATS-R9 oligo-peptoplexes and incubated for 24 h. H9c2 and HEK293 cell lines were used as controls. The H9c2 and HEK293 cells were treated with FITC conjugated ATS-R9 (25 μg/ml) oligo-peptoplexes and incubated for 24 h.

Gel Retardation Assay

1 μg of luciferase plasmid DNA (p-β-Luci, Promega (USA)), deionized water, and ATS-R9 (charge ratios: 0.25, 0.5, 1, 3, 5, 7, and 9) were incubated for 30 min at room temperature to construct oligo-peptoplexes. The oligo-peptoplexes were subjected to electrophoresis under 0.5% TBE buffer solution in 0.8% agarose gel for 25 min (100 V). Naked DNA was used as a control. The DNA condensation efficiency of the ATS-R9 was compared with that of branched PEI (25 KDa, Sigma, USA).

Zeta Potential and Size Measurement

5 μg of luciferase plasmid DNA (p-β-Luci), deionized water, and ATS-R9 (charge ratios: 0.5, 1, 3, 5, 7, and 9) were incubated for 30 min at room temperature to construct oligo-peptoplexes. The mean diameters and surface zeta potentials of the oligo-peptoplexes were measured using DLS equipped with a Zetasizer-Nano ZS (Malvern Instruments, UK).

In Vitro Transfection Efficiency

A luciferase assay kit was purchased from Promega (USA). A DC protein assay kit and bovine serum albumin standard were purchased from Bio-Rad Laboratories (USA). 3T3-L1 preadipocytes and differentiated adipocytes were seeded in 24 well plates.

Oligo-peptoplexes were prepared by mixing ATS-9R and 2 μg of luciferase plasmid DNA at a charge ratio of 5. R9 and PEI polyplexes were used as controls and prepared at a charge ratio of 5. The cells were transfected after 24 h of seeding.

After 72 h of incubation, the cells were washed with PBS and treated with 150 μl of 1× cell lysis buffer reagent for 20 min. The cell lysates were then scraped, harvested, transferred to 1.5 ml microtubes, and centrifuged for 3 min at 13,000 rpm.

The luminescence of the cell lysates was measured on a 96-well plate luminometer (Berthold Detection Systems, Germany) with 20-second integration and expressed as relative luminescence units (RLU)/mg of cell protein. Protein concentration was determined by the DC protein assay kit with bovine serum albumin standard.

In Vitro Cytotoxicity Assay

Cell viability was measured by MTT [3-(4,5-dimethylthiazol-2-yl)-2,5-diphenyltetrazolium bromide]assay.

3T3-L1 differentiated adipocytes were incubated in 24-well plates. The adipocytes (at day 10) were treated with oligo-peptoplexes prepared by luciferase plasmid DNA, plain DMEM medium, and ATS-9R at predetermined charge ratios. PEI polyplexes were used as the control.

After 48 h of transfection, 50 μl of MTT reagent was added to 500 μl medium in each well and incubated for 3 h at 37° C. The culture media were removed and 500 μl dimethyl sulfoxide (DMSO) was added to each well and incubated for 20 min at room temperature. Absorbance was measured at 570 nm.

Obesity Induction in Mouse Model

C57BL/6J mice at 3 weeks of age were purchased from Central Lab Animal Inc. (Korea). For the first two weeks, the mice were fed 50% normal diet and 50% rodent diet with 60 kcal % from fat. The proportion of high fat diet fed to the mice was gradually increased and beginning in week 7, the mice were fed only a high fat diet with 60 kcal % from fat. The mice became obese after week 14 (body weight>45 g).

In Vivo Fat Homing

FITC conjugated ATS-9R (10 mg/ml) and FITC-9R (10 mg/ml) were diluted in PBS to a final concentration of 1.5 mg/ml and 100 μl of peptide was injected into obese mice by tail vein injection. Immediately after injection, peptide localization in vasculatures of different organs was observed by Cellvizio (Mauna Kea Technologies, France).

EXAMPLE 1

Differentiation of 3T3-L1 Preadipocytes

The stages of 3T3-L1 adipocyte differentiation are shown in FIG. 2.

When 3T3-L1 preadipocytes were incubated in a medium for adipocyte differentiation, the cell morphology was changed gradually to round-shaped and large lipid droplets in the cytoplasm. About 90% of the cell region was filled with the lipid droplets (FIG. 2b).

As a result of Oil red O staining, 95% of the cell culture population was differentiated into mature adipocytes (FIG. 2c). Oil red O staining is a commonly used technique to confirm adipocyte differentiation due to its ability to selectively stain neutral lipids. Higher Oil Red O accumulation represents higher adipocyte differentiation.

For quantitative analysis, the differentiated adipocytes were stained with Oil red O for 5-14 days. Accumulated Oil red O was eluted and quantified by spectrophotometry at 520 nm. The results are shown in FIG. 2d. The Oil Red O accumulation increased with increasing cell differentiation time. The time-dependent increase in the amount of Oil red O indicates that the preadipocytes were continuously differentiated into mature adipocytes with time.

EXAMPLE 2

Internalization of ATS-R9 into Adipocytes

To monitor the degree of internalization of ATS-R9 into cells, mature adipocytes and preadipocytes were treated with FITC-labeled ATS-R9 (FITC-ATS-R9) and the delivery of the support to the cells was investigated.

3T3-L1 differentiated adipocytes (at day 10) were treated with FITC-conjugated ATS-R9 (25 µg/ml) and incubated for predetermined periods. The plasma membranes of the cells were stained with Cellmask Deep Red and the nuclei were counterstained with DAPI. Blue channel (for DAPI) is depicted as white to show nuclear localization of ATS-R9. Images were captured with a confocal laser scanning microscope. Scale bar: 10 µm.

As a result, ATS-R9 was very fast internalized into the 3T3-L1 adipocytes. ATS-R9 reached the cytoplasm and nuclei within 15 min and 1 h, respectively, and strong fluorescence signals were maintained until 48 h.

This is due to the ability of ATS-R9 to target adipocytes through prohibitin, which has already been explained. Upon internalization into 3T3-L1 mature adipocytes, the fused peptide passed rapidly through the nuclear membranes. That is, ATS-R9 was delivered very fast to the cells. The time-dependent intracellular distributions of ATS-R9 are shown in FIG. 3.

ATS-R9 reached the cytoplasm and nuclei in the mature adipocytes within 15 min and 1 h, respectively, and maintained its steady state for 48 h. In contrast, ATS-R9 maintained its steady state after 48 h in the preadipocytes and its migration to the nuclei was observed after 48 h.

From these results, it can be concluded that the different uptake patterns and distributions of ATS-R9 in mature adipocytes and preadipocytes are associated with different prohibitin levels and locations.

EXAMPLE 3

Competition Assay

Competition assay was conducted to investigate the influence of ATS on the targeting of ATS-R9 to adipocytes.

3T3-L1 preadipocytes and mature adipocytes were treated with free ATS at day 10 and the receptor was blocked for 6 h.

The cells were incubated in the presence or absence of free ATS. All cells were treated with FITC-ATS-R9/pLuc complexes [also called "oligo-peptoplexes (oligo-peptide/ DNA complexes)"].

In order to demonstrate a specific binding affinity of ATS-R9 for adipocytes, HEK293 and H9c2 cells, in which prohibitin was not expressed on the plasma membranes, were used as controls. The cells were treated with FITC conjugated ATS-R9 oligo-peptoplexes and incubated for 24 h.

The results are shown in FIG. 4. The pretreatment with free ATS suppressed internalization of the ATS-R9 oligo-peptoplexes. This suggests that the ATS-R9 oligo-peptoplexes were internalized into the cells through prohibitin.

A group incubated with free ATS in 3T3-L1 preadipocytes or mature adipocytes showed a considerably low level of FITC intensity compared to a group incubated without free ATS (FIGS. 4a and 4c). This is because a small amount of FITC-ATS-R9 can penetrate the cell membranes and can be internalized into the cells. The difference in FITC intensity between the two groups is due to the blocking of prohibitin by pre-culture with free ATS. Prohibitin bound to free ATS does not freely interact with the ATS-R9/pLuc oligo-peptoplexes, resulting in reduced internalization of the oligo-peptoplexes. Similar results were observed in the preadipocytes. However, the difference in fluorescence intensity was smaller than that observed in the mature adipocytes. Such results are attributed to different prohibitin levels observed in the mature adipocytes and preadipocytes.

Small amounts of peptides were located in HEK293 and H9c2 cells, in which prohibitin was not expressed, compared to in adipocytes treated with the same amount of peptides for the same incubation time (FIG. 4b). Since weak FITC intensity was observed in each cell line, it appears that a very small amount of ATS-R9/DNA oligo-peptoplexes were internalized in these cells.

Furthermore, such results showed that ATS-R9 targeted and recognized adipocytes independent of differentiation state and was internalized into the cells through the prohibitin-mediated mechanism. That is, these results demonstrate a specific binding affinity of ATS-R9 for adipocytes.

EXPERIMENTAL EXAMPLE 1

Confirmation of Ability to Target Adipocytes Depending on the Degree of Differentiation To investigate the location and amount of prohibitin expressed depending on the degree of adipocyte differentiation, two types of adipocytes were treated with rhodamine B-labeled ATS (RhoB-ATS). ATS could be used to determine the presence of prohibitin instead of antibody due to its high ability to bind to prohibitin.

Through this experiment, prohibitin, an ATS receptor, present in mature adipocytes and preadipocytes was observed to be distributed in different profiles depending on the degree of differentiation.

The results are shown in detail in FIG. 5. That is, the ability of ATS to target adipocytes before differentiation (preadipocytes) and adipocytes after differentiation (obese adipocytes) could be confirmed.

Binding of ATS to prohibitin was determined by an immunoprecipitation assay (FIG. 5a) and the distributions of prohibitin in 3T3-L1 preadipocytes and mature adipocytes were confirmed through the staining results (FIGS. 5b and 5c). FIG. 5b reveals that ATS was effectively delivered to the differentiated obese adipocytes and FIG. 5c reveals a difference in the expression of prohibitin, an ATS ligand.

As demonstrated above, prohibitin was highly expressed in the plasma membranes, cytoplasm, and nuclei of the mature adipocytes, and primarily showed a low expression level in the cytoplasm of the preadipocytes. The difference in prohibitin distribution indicates different intracellular ATS-R9 delivery and distribution mechanisms in mature adipocytes and preadipocytes.

In conclusion, the targeting efficiency of ATS to adipocytes before differentiation is not significantly high but that of ATS to obese cells after differentiation is very high.

COMPARATIVE EXAMPLE 1

Confirmation of Prohibitin Expression in Non-Obese (Mature) Adipocytes and Myocytes To more clearly demonstrate that the inventive fused oligo-peptoplexes have specificity for obese adipocytes, the expression profiles of prohibitin in non-obese mice and myocytes were compared and analyzed. Western blotting was used for analysis. The results are shown in FIG. 6.

Particularly, there was a significant difference in the expression profile of prohibitin between the non-obese and obese mice, as shown in FIG. 6a, and there was a clearly large difference in the expression profile of prohibitin in the myocytes, as shown in FIG. 6b. That is, the expression of prohibitin in the non-obese adipocytes was higher than that in the obese adipocytes. It was also confirmed that prohibitin was expressed specifically to the cell membranes in the obese adipocytes, unlike in the myocytes. These results demonstrate that an increase in the expression of prohibitin specific to cell membranes leads to an increase in the targeting efficiency of ATS to adipocytes.

EXAMPLE 5

Physical and Biological Characterization of the Oligo-Peptoplexes

The biochemical properties of the cationic polymer/DNA complexes are major factors affecting the cellular uptake, cargo stability, cytotoxicity, and transgenic expression thereof. The ability of ATS-R9 to condense and protect DNA was confirmed by a gel retardation assay and the degradation of DNA in mouse serum was tested.

5-1. Gel Retardation Assay and Serum Protection Assay

The condensation efficacy of ATS-R9 was compared with that of branched PEI (25 kDa).

Oligo-peptoplexes were prepared with luciferase plasmid DNA (p-β-Luci), deionized water, and ATS-R9 or PEI with predetermined charge ratios and incubated for 30 min at room temperature.

Oligo-peptoplexes were prepared at predetermined charge ratios, mouse serum was added to the polyplexes at a final concentration of 50% (vol/vol), and the samples were incubated for 2 h at 37° C.

For the decomplexation of DNA from the polyplexes after serum incubation, heparin in phosphate-buffered saline (pH 7.4, 0.5 mol/l NaCl) was added to the samples in the presence of 0.01 mol/l EDTA and incubated for 1 h. The samples were loaded in 0.8% agarose gel.

As a result, DNA migration was observed in neither ATS-R9 nor PEI at a charge ratio of ≥3, indicating complete DNA condensation (FIG. 7a). ATS-R9 protected DNA from degradation in serum at the optimum charge ratio whereas naked DNA was completely degraded under the test conditions (FIG. 7b).

In other words, ATS-R9 can efficiently condense the plasmid DNA and protects DNA from degradation in serum. The formation of positively charged smaller complexes from the DNA complexes enables efficient internalization into cells.

5-2. Zeta Potential and Size Measurement

The zeta potentials and mean diameters of the ATS-R9/DNA oligo-peptoplexes were measured using dynamic light scattering (DLS).

As a result, the oligo-peptoplexes had positive zeta potentials at charge ratios of ≥3 and mean diameters of less than 200 nm at charge ratios of ≥1, as shown in FIG. 8.

5-3. Cell Viability Analysis

The toxicity of the ATS-R9/DNA oligo-peptoplexes was tested. 3T3-L1 differentiated adipocytes at day 10 were transfected with the oligo-peptoplexes. After 48 h of transfection, cell viability was analyzed by MTT assay (n=6).

As a result, the differentiated adipocytes showed a cell viability of at least 90% at a charge ratio up to 9, as shown in FIG. 9. This indicates that the oligo-peptoplexes are non-toxic to the differentiated adipocytes compared to toxic PEI.

EXAMPLE 6

Transfection Efficiency 6-1. Optimization of Charge Ratio

A charge ratio for the optimization of transfection efficiency was investigated. Mature adipocytes at day 10 of differentiation were transfected with p-β-Luci by ATS-R9, R9, and PEI at a charge ratio of 5. Luciferase gene expression was measured after 72 h by a luciferase assay kit.

As a result, the transfection efficiency of the ATS-R9 oligo-peptoplexes at a charge ratio of 5 was found to be higher than those of R9 and PEI (FIG. 10a). That is, ATS-R9 had a higher transfection efficiency at the same charge ratio than R9 and PEI. The transfection efficiency and gene expression efficiency increased with increasing adipocyte differentiation time.

6-2. Optimum Time Point

To determine an optimum transfection time point, 3T3-L1 differentiated adipocytes were transfected with luciferase plasmid DNA (p-β-Luci) by ATS-R9 and PEI at a charge ratio of 5 at different days of differentiation. Luciferase gene expression was measured after 72 h by a luciferase assay kit.

As a result, higher gene expression was obtained at 9 and 10 days of differentiation, suggesting that the oligo-peptoplexes are suitable for the transfection of mature adipocytes (FIG. 10b).

EXAMPLE 7

In Vivo Fat Homing Experiment

In this example, in vivo experiments were conducted using diet-induced obesity (DIO) mice. FITC-ATS-R9 was administered to the obese mice by tail vein injection to observe the targeting of the ATS-R9 to adipose tissue. Tracking was visualized using probe-based confocal laser endomicroscopy (pCLE, Cellvizio).

The liver, kidney, and other fat pad vasculatures of each mouse were observed. As a result, ATS-R9 aggregated in the fat pad vasculatures. In the other organs, ATS-R9 floated along the blood vessels and no aggregation was observed (FIG. 11).

The fat homing of FITC-conjugated ATS-R9 in fat pad vasculature was compared with that of FITC-conjugated R9. As a result, ATS-R9 aggregated in the fat pad vasculature, unlike R9. That is, upon R9 administration, aggregation was not observed in the fat vasculatures but was observed on the endothelia (FIG. 12).

The fat pad microvessels were horizontally cut and analyzed. The images of the fat pad microvessels were obtained at fixed distances from the probe to the vasculatures. The ATS-R9 treatment generated highly accumulated fluorescence intensities at the endothelial edges while the R9 treatment generated fluorescence intensities over the entire region of the vasculatures (FIG. 13). That is, as a result of comparing the fat homing of FITC-conjugated ATS-R9 with that of R9 in the fat pad microvessels, ATS-R9 was bound to the fat pad microvessels but no binding of R9 to the fat pad microvessels was observed.

This is because ATS-R9 binds to the fat vasculatures to form aggregates in the vascular endothelia. In contrast, ATS-R9 migrates continuously along the blood vessels without binding or aggregation, which is a typical ATS-R9-endothelia interaction in the liver and kidney.

As can be seen from the above results, ATS-R9 can selectively bind to adipose tissue vasculatures, aggregates only in blood vessels and adipose tissue microvessels, and does not aggregate in other organs, such as liver and kidney. The binding pattern of ATS-R9 in adipose tissue is completely different from that of the simple arginine binding structure.

EXAMPLE 8

In Vivo Gene Expression

First, internalization of ATS-R9 into in vivo adipose tissues was investigated.

FITC-conjugated ATS-R9 was administered to C57BL/6J obese mouse by tail vein injection. Rhodamine-conjugated lectin was injected to stain blood vessels.

Fixed adipose tissue sections were imaged and observed using a multiphoton confocal laser scanning microscope. As a result, ATS-R9 penetrated the blood vessels and was gradually internalized into adipocytes (FIG. 14a). The white arrows indicate FITC-ATS-R9 internalized into adipocytes (scale bar: 50 µm).

Next, the ability to induce the FITC-ATS-R9 into adipose tissues (adipose tissue targeting ability or homing) was confirmed by an immunofluorescence assay.

FITC-conjugated ATS-R9 was injected into C57BL/6J obese mice and fixed adipose tissue sections were incubated with biotin-conjugated anti-FITC antibody. Cy3-conjugated ExtrAvidin was used for signal amplification thereof. Images were observed using a multiphoton confocal laser scanning microscope. FIG. 14b confirms the induction of FITC-ATS-R9 into adipose tissues (adipose tissue homing).

Finally, in vivo gene expression was confirmed. To this end, red fluorescence protein (RFP) expressing plasmid was concentrated by FITC-ATS-R9 and the oligo-peptoplexes were injected into C57BL/6J obese mice. Non-treated mice were used as controls. Images were observed using a multiphoton confocal laser scanning microscope. As a result, RFP gene expression was clearly confirmed (FIG. 14c).

EXAMPLE 9

Ability to Deliver Sh-RNA and Silent Gene

A determination was made as to whether the inventive ATS-R9 is effective in the in vitro and in vivo delivery of sh-RNA and silent gene to adipocytes.

First, 3T3-L1 mature adipocytes were transfected with 2 µg of fabp4 sh-RNA by ATS-R9, PEI, and lipofectamine and gene silencing efficiency was measured by RT-PCR. GAPDH was used as an endogenous control. As a result, the Fabp4 gene silencing efficiency was 70% or more (FIG. 15).

9-1. Weight Reduction Effect

After sh-FABP4 treatment, body weight reduction was also confirmed (FIG. 16).

C57BL/6J mice were treated with 30 µg of sh-FABP4, together with ATS-R9, twice weekly for 8 weeks and the oligo-peptoplexes were injected subcutaneously thereinto. sh-Luci was used as a control.

After 8 weeks, the group treated with the sh-FABP4-ATS-R9 oligo-peptoplexes lost about 20% of its original weight.

9-2. Insulin and Glucose Tolerance Test

Insulin and glucose tolerances were observed.

C57BL/6J mice were treated with the sh-FABP4-ATS-R9 oligo-peptoplexes twice weekly for 8 weeks. The oligo-peptoplexes were administered subcutaneously. sh-Luci was used as a control.

After 8 weeks, the groups treated with the sh-FABP4-ATS-R9 oligo-peptoplexes were confirmed to be more sensitive to insulin and glucose (FIGS. 17 and 18).

That is, the inventive ATS-R9 was effective in the in vitro and in vivo delivery of sh-RNA and silent gene to adipocytes, led to a weight reduction when the therapeutic gene for the treatment of obesity and obesity-induced metabolic syndromes was delivered, and contributed to an improvement in insulin and glucose sensitivity.

COMPARATIVE EXAMPLE 2

Comparison of Gene Delivery Ability (1) Gene Delivery Abilities of Other Delivery Systems to Adipocytes The ability of ATS-R9 to deliver luciferase gene to obese adipocytes was evaluated. PEI and lipofectamine were used as controls. The results are shown in FIG. 19.

As a result, the gene delivery efficacy of ATS-R9 to obese adipocytes was confirmed to be superior to those of the other delivery systems PEI and lipofectamine.

(2) Gene Delivery Abilities Before and after Adipocyte Differentiation

Gene delivery efficacies before and after adipocyte differentiation were compared. The results are shown in FIG. 20.

These results confirm that as differentiation of adipocytes into obese adipocytes proceeded, the gene delivery efficacy of the inventive ATS-R9 increased.

(3) Gene Delivery Ability According to Sequence Specificity

Luciferase was used as a gene to be delivered and scrambled ATS was used as a fat-targeting sequence. The ability of (scrambled ATS)-R9 to deliver the gene to obese adipocytes was compared to that of ATS-R9.

As a result, the use of the scrambled ATS greatly reduced the ability to deliver the gene, as shown in FIG. 21.

INDUSTRIAL APPLICABILITY

As is evident from the foregoing, the ATS-R9 peptide structure of the present invention can directly target mature obese adipocytes through the mechanism of overexpression of prohibitin in adipocytes after differentiation to deliver a gene to the adipocytes. Due to this specific function and effect, the ATS-R9 peptide structure of the present invention would be very useful in gene therapy for obesity.

The invention claimed is:

1. A complex comprising an adipocyte-targeting sequence (ATS), a nona-arginine (R9) peptide comprising the sequence of SEQ ID NO: 4, and an adipocyte-targeting therapeutic gene for the treatment of obesity and obesity-induced metabolic syndromes, wherein the adipocyte-targeting sequence consists of the amino acid sequence of SEQ ID NO: 1.

2. The complex according to claim 1, wherein the adipocyte-targeting sequence and the nona-arginine (R9) peptide bind to prohibitin.

3. The complex according to claim 1, wherein the nona-arginine (R9) peptide has a Cys-(D-R)9-Cys structure comprising the sequence of SEQ ID NO: 3.

4. The complex according to claim 1, wherein the therapeutic gene for the treatment of obesity and obesity-induced metabolic syndromes is RNAi.

5. The complex according to claim 4, wherein the RNAi is siRNA or shRNA.

6. The complex according to claim 1, wherein the complex has a diameter of 200 nm or less.

7. The complex according to claim 1, wherein the complex has a charge ratio (+/−) of 3:1 to 8:1.

8. A method of delivering an adipocyte-targeting therapeutic gene to adipocytes comprising administering the complex according to claim 1, to said adipocytes, wherein the adipocytes are differentiated mature obese adipocytes.

9. The method according to claim 1, wherein the adipocytes are mature obese adipocytes at 9 to 11 days after initiation of differentiation.

10. A composition for the treatment of obesity or obesity-induced metabolic syndromes comprising the complex according to claim 1 as an active ingredient.

* * * * *

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide: adipocyte targeting sequence

<400> SEQUENCE: 1

Cys Lys Gly Gly Arg Ala Lys Asp Cys
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide: adipocyte targeting
      sequence - R9

<400> SEQUENCE: 2

Cys Lys Gly Gly Arg Ala Lys Asp Arg Arg Arg Arg Arg Arg Arg Arg
1               5                   10                  15

Arg Cys

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide: Cys-(D-R)9-Cys

<400> SEQUENCE: 3

Cys Arg Arg Arg Arg Arg Arg Arg Arg Arg Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide: R9

<400> SEQUENCE: 4

Arg Arg Arg Arg Arg Arg Arg Arg Arg
1               5
```